United States Patent [19]

Kelly

[11] Patent Number: 5,032,312
[45] Date of Patent: Jul. 16, 1991

[54] 3E-CYCLOHEXYLALKOXY DERIVATIVES

[75] Inventor: Stephen Kelly, Möhlin, Switzerland

[73] Assignee: Hoffmann-La Roche Inc., Nutley, N.J.

[21] Appl. No.: 487,096

[22] Filed: Mar. 2, 1990

[30] Foreign Application Priority Data

Apr. 20, 1989 [CH] Switzerland .................. 1547/89

[51] Int. Cl.$^5$ ............... C09K 19/30; C07D 401/00; C07D 405/00; C07D 491/00
[52] U.S. Cl. .............. 252/299.01; 252/299.61; 252/299.63; 544/239; 544/315; 544/408; 549/21; 549/28; 549/416; 549/421; 546/266; 546/343; 568/579; 568/626; 568/659; 568/664
[58] Field of Search ............. 252/299.01, 299.61, 252/299.63, 299.62, 299.64, 299.65, 299.66, 229.60; 568/664, 665, 659, 626, 579, 657, 656, 655, 647, 642, 634, 632, 631, 630, 588, 585, 584; 544/239, 408; 549/21, 28, 372, 378, 416, 421; 546/266, 343

[56] References Cited

U.S. PATENT DOCUMENTS

| | | | |
|---|---|---|---|
| 3,840,529 | 10/1974 | Maruyama et al. | 260/240 R |
| 4,035,056 | 7/1977 | Coates et al. | 350/160 |
| 4,627,933 | 12/1986 | Eidenschink et al. | 252/299.6 |
| 4,891,491 | 1/1990 | Hoelderich et al. | 568/691 |

FOREIGN PATENT DOCUMENTS 104327 4/1984 European Pat. Off. .
3509170 9/1985 Fed. Rep. of Germany .

OTHER PUBLICATIONS

Derwent Abstract 86-252836/39.
Japanese Abstact J6 2286-941-A, Dec. 1987, "4-Substd.-Cyclohexyl Crotyl Ether Deriv. Used For Nematic LC cpds. Can Be Obtd. From . . . ".
Japanese Abstract J6 2286-942-A, Dec. 1987, "New 4-Substd. Phenyl:Crotyl:Ether Deriv.-Used In Electro-Optical Devices, Has High N-1 Points and Wide Drive Temp. . . . ".
Japanese Abstract J6 2286-943-A, Dec. 1987, "4-Substd. Biophenyl Crotyl Ether Deriv.-Used For New Nematic Liq. Crystal Cpds., for Electro:Optical Display . . . ".

Primary Examiner—Robert L. Stoll
Assistant Examiner—Greg M. Sweet
Attorney, Agent, or Firm—George M. Gould; George W. Johnston; Alan P. Kass

[57] ABSTRACT

Compounds of the formula

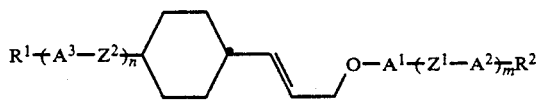

I wherein $R^1$ denotes a group $R^3$ or $R^3$—$A^4$—$Z^3$— and $R^2$ denotes a group $R^4$ or —$Z^4$—$A^5$—$R^4$; m and n each individually stand for the number 0 or 1; $A^1$, $A^2$, $A^3$, $A^4$ and $A^5$ each independently represent unsubstituted or halogen-, cyano- and/or methyl-substituted 1,4-phenylene in which optionally 1 CH group or 2 CH groups is/are replaced by nitrogen, trans-1,4-cyclohexylene in which optionally 2 non-adjacent methylene groups are replaced by oxygen and/or sulphur, 1-cyano-trans-1,4-cyclohexylene, bicyclo[2.2.2]octane-1,4-diyl, naphthalene-2,6-diyl, tetralin-2,6-diyl or trans-decalin-2,6-diyl; $Z^1$, $Z^2$, $Z^3$ and $Z^4$ each independently signify a single covalent bond, —COO—, —OOC—, —CH$_2$O—, —OCH$_2$—, —CH$_2$CH$_2$, —C≡C—, —(CH$_2$)$_3$O—, —O(CH$_2$)$_3$— or the trans form of —CH=CH—CH$_2$O— or —OCH$_2$—CH=CH—; $R^3$ and $R^4$ each independently denote halogen, cyano, —NCS, —CF$_3$, —OCF$_3$ or alkyl in which optionally one <CH—CH> is replaced by <C=C> and/or optionally one methylene group or two non-adjacent methylene groups is/are replaced by —O—, —COO— and/or —OOC— and/or optionally one methylene group is replaced by —CHX—; and X signifies halogen, cyano or methyl, as well as liquid crystalline mixtures and their use for electro-optical purposes.

23 Claims, No Drawings

3E-CYCLOHEXYLALKOXY DERIVATIVES

BACKGROUND

1. Field of the Invention

The present invention is concerned with novel compounds having a trans-3-cyclohexylallyloxy group, liquid crystalline mixture which contain such compounds and their use for electro-optical purposes.

2. Description

Liquid crystals are used primarily as dielectrics in indicating devices, since the optical properties of such substances can be influenced by an applied voltage. Electro-optical devices based on liquid crystals are well-known to the Person skilled in the art and can be based on various effects. Examples of such devices are cells having dynamic scattering, DAP cells (deformation of aligned phases), guest/host cells, TN cells ("twisted nematic") and STN cells ("super-twisted nematic") having a twisted nematic structure, SBE cells ("super birefringence effect"), phase change cells having a cholesteric-nematic phase transition and OMI cells ("optical mode interference"). The most common indicating devices are based on the Schadt-Helfrich effect and have a twisted nematic structure.

Further, electro-optical devices based on chiral tilted smectic liquid crystals have been proposed in Appl. Phys Lett. 36, 899 (1980) and in Recent Developments in Condensed Matter Physics 4, 309 (1981). In this case the ferroelectric properties of these materials are utilized. As the tilted smectic Phases there are suitable, for example, smectic C, F, G, H, I and K phases. There are generally preferred smectic C phases which Permit especially high response speeds. The chiral tilted phases are usually denoted by $S_C^*$, $S_F^*$ etc., with the asterisk indicating the chirality.

The liquid crystal materials must have a good chemical and thermal stability and a high stability towards electric fields and electromagnetic radiation. Further, the liquid crystal materials should have low viscosity and in the cells should give short resPonse times, low threshold potentials and a high contrast. Furthermore, at the usual operating temperatures they should have a suitable mesophase, for example a nematic, cholesteric or chiral tilted smectic phase. Further properties such as the electrical conductivity, the dielectric anisotropy and the optical anisotropy must fulfil different requirements depending on the type of cell and field of application. For example, materials for cells having a twisted nematic structure should have a positive dielectric anisotropy and an electrical conductivity which is as low as possible. Besides the general interest in liquid crystal materials having a high optical anisotropy, there has recently been an increased interest in materials having a low optical anisotropy, especially for actively addressed liquid crystal indicators, e.g. in the case of TFT applications (thin film transistor) in television sets. On the other hand, chiral tilted smectic liquid crystals should have a sufficiently high spontaneous polarization, but a comparatively small twisting. The pitch of the twisting should preferably be significantly larger than the plate separation of the cell which is used and should typically amount to at least about 10 μm in order to provide bistable displays having good switching.

In order to optimize the properties, liquid crystals are generally used as mixtures of several components. It is therefore important that the components have a good miscibility with one another. Cholesteric mixtures can preferably consist of one or more optically active doping substances and a nematic liquid crystal material. Ferroelectric liquid crystals can preferably consist of one or more optically active doping substances and a liquid crystal material having a tilted smectic phase.

SUMMARY OF THE INVENTION

The present invention provides the compounds of the formula

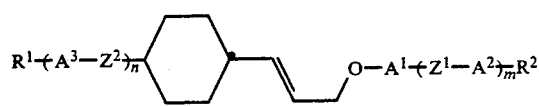

wherein $R^1$ denotes a group $R^3$ or $R^3$-$A^4$-$Z^3$— and $R^2$ denotes a group $R^4$ or -$Z^4$-$A^5$-$R^4$; m and n each individually stand for the number 0 or 1; $A^1$, $A_2$, $A^3$, $A^4$ and $A^5$ each independently represent unsubstituted or halogen-, cyano- and/or methyl-substituted 1,4-phenylene in which optionally 1 CH group or 2 CH groups is/are replaced by nitrogen, trans-1,4-cyclohexylene in which optionally 2 non-adjacent methylene groups are replaced by oxygen and/or sulphur, 1-cyano-trans-1,4-cyclohexylene, bicyclo[2.2.2]octane-1,4-diyl, naphthalene-2,6-diyl, tetralin-2,6-diyl or trans-decalin-2,6-diyl; $Z^1$, $Z^2$, $Z^3$ and $Z^4$ each independently signify a single covalent bond, —COO—, —OOC—, —CH$_2$O—, —OCH$_2$—, —CH$_2$CH$_2$—, —C≡C—, —(CH$_2$)$_3$O—, —O(CH$_2$)$_3$— or the trans form of —CH=CH—CH$_2$O— or —OCH$_2$—CH=CH—; $R^3$ and $R^4$ each independently denote halogen, cyano, —NCS, —CF$_3$, —OCF$_3$ or alkyl in which optionally one >CH—CH< is replaced by >C=C< and/or optionally one methylene group or two non-adjacent methylene groups is/are replaced by —O—, —COO— and/or —OOC— and/or optionally one methylene group is replaced by —CHX—; and X signifies halogen, cyano or methyl.

In spite of the comparatively high flexibility of the trans-3-cyclohexylallyloxy group, the compounds of formula I have a pronounced tendency to form liquid crystalline phases. The optically inactive compounds of formula I have for the most part a nematic, a smectic A and/or a tilted smectic (primarily $S_C$) phase and the optically active compounds of formula I have for the most part a cholesteric, a smectic A and/or a chiral tilted smectic (primarily $S_C^*$) phase. These mesophase types are o especially suitable for producing nematic, cholesteric or chiral tilted smectic phases in liquid crystal mixtures. The present invention therefore provides a wide range of novel components and mixtures for the usual electro-optical fields of application of liquid crystals.

DETAILED DESCRIPTION OF THE INVENTION

The present invention concerns compounds of the formula

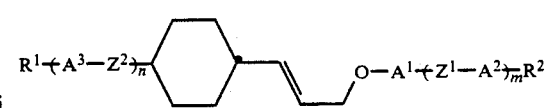

wherein $R^1$ is $R^3$ or $R^3$—$A^4$—$Z^3$—and $R^2$ is $R^4$ or —$Z^4$—$A^5$—$R^4$; each of m and n individually is the integer 0 or 1; each of $A^1$, $A^2$, $A^3$, $A^4$ and $A^5$ independently is 1,4-phenylene which is unsubstituted or substituted with one or more of halogen, cyano or methyl, said unsubstituted or substituted 1,4-phenylene as defined above wherein one of its CH group or two CH groups are replaced by nitrogen, trans-1,4-cyclohexylene, trans-1,4-cyclohexylene in which two non-adjacent methylene groups are replaced by at least one of oxygen or sulphur, 1-cyano-trans-1,4-cyclohexylene, bicyclo[2.2.2]octane-1,4-diyl, naphthalene-2,6-diyl, tetralin-2,6-diyl or trans-decalin-2,6-diyl; each of $Z^1$, $Z^2$, $Z^3$ and $Z^4$ independently is a single covalent bond, —COO—, —OOC—, —CH$^2$O—, —OCH$_2$—, —CH$_2$CH$_2$—, —C≡C—, —(CH$_2$)$_3$O—, —O(CH$_2$)$_3$— or the trans configuration of either —CH=CH—CH$_2$O— or —OCH$_2$—CH=CH—; each of $R^3$ and $R^4$ independently is halogen, cyano, —NCS, —CF$_3$, —OCF$_3$, alkyl or alkyl in which one or more of its carbon atoms are replaced as follows: one >CH—CH< is replaced by >C=C<, one methylene group or two non-adjacent methylene groups are replaced by at least one of —O—, —COO— and —OOC—, or one methylene group is replaced by —CHX—; and X is halogen, cyano or methyl.

In spite of the comparatively high flexibility of the trans-3-cyclohexylallyloxy group, the compounds of formula I have a pronounced tendency to form liquid crystalline phases. The optically inactive compounds of formula I have for the most part a nematic, a smectic A and/or a tilted smectic (primarily $S_C$) phase and the optically active compounds of formula I have for the most part a cholesteric, a smectic A and/or a chiral tilted smectic (primarily $S_C^*$) phase. These mesophase types are especially suitable for Producing nematic, cholesteric or chiral tilted smectic Phases in liquid crystal mixtures The present invention therefore Provides a wide range of novel components and mixtures for the usual electro-optical fields of application of liquid crystals.

The compounds of formula I have a high chemical stability and a high stability towards electric and magnetic fields. They are colourless, can be manufactured readily and have a very good solubility with one another and in known liquid crystal materials. Further, they have low viscosities and give short response times in indicating devices.

The properties of the compounds of formula I can be varied in wide ranges depending on the number and significance of the rings and of the substituents. For example, aromatic rings lead to higher values of the optical anisotropy and saturated rings lead to lower values of the optical anisotropy. An increase in the clearing point can be achieved, for example, by introducing one or more additional rings. Polar terminal groups such as cyano, halogen, —NCS, —CF$_3$ or —OCF$_3$ and rings such as pyrimidine-2,5-diyl, trans-1,3-dioxane-2,5-diyl etc. increase the dielectric anisotropy, rings such as pyridazine-3,6-diyl, 1-cyano-trans-1,4-cyclohexylene, 2,3-dicyano-1,4-phenylene etc. reduce the dielectric anisotropy and lateral halogen and cyano substituents contribute to the dielectric constants not only parallel to but also perpendicular to the longitudinal axis of the molecule, which, depending on the substitution pattern, can be used to increase or reduce the dielectric anisotropy. Further, the mesophase range can be modified, a possible tendency to form highly ordered smectic phases can be largely suppressed and frequently the solubility can be improved by lateral substituents on one or more rings. Furthermore, the elastic properties, the threshold potentials, the response times, the mesophases etc. can be modified further by a C=C double bond in the side-chain.

The compounds in accordance with the invention therefore permit a further optimization of liquid crystal mixtures and a modification of the electro-optical properties in a wide range depending on the properties desired.

The term "halogen" denotes in the scope of the present invention fluorine, chlorine, bromine or iodine, especially fluorine or chlorine.

The term "unsubstituted or halogen-, cyano- and/or methyl-substituted 1,4-phenylene in which optionally 1 CH group or 2 CH groups is/are replaced by nitrogen" or the term "1-4-phenylene which is unsubstituted or substituted with one or more of halogen, cyano or methyl, said unsubstituted or substituted 1,4-phenylene wherein one its CH group or two CH groups are replaced by nitrogen" embraces groups such as 1,4-phenylene, 2-fluoro-1,4-phenylene, 2,3-difluoro-1,4-phenylene, 2-chloro-1,4-phenylene, 2-bromo-1,4-phenylene, 2-cyano-1,4-phenylene, 2,3-dicyano--1,4-phenylene, 2-methyl-1,4-phenylene, pyridine-2,5-diyl, pyrazine-2,5-diyl, pyrimidine-2,5-diyl, pyridazine-3,6-diyl and the like. Preferred groups are 1,4-phenylene, 2-fluoro-1,4-phenylene, 2,3-difluoro-1,4-phenylene, pyridine-2,5-diyl, pyrazine-2,5-diyl and pyrimidine-2,5-diyl.

The term "trans-1,4-cyclohexylene in which optionally 2 non-adjacent methylene groups are rePlaced by oxygen and/or sulphur" or the term "trans-1,4-cyclohexylene. trans-1,4-cyclohexylene in which two non-adjacent methylene groups are rePlaced by at least one of oxygen or sulphur" embraces groups such as trans-1,4-cyclo-hexylene, trans-1.3-dioxane-2.5-diyl and trans-1,3-dithiane-2,5-diyl.

The term "tetralin-2,6-diyl" denotes 1,2,3,4-tetrahydronaphthalene-2,6-diyl. The term "decalin-2,6-diyl" embraces 2,6-disubstituted groups derived from decahydronaphthalene, especially (4aαH,8aβH)-decahydronaphthalene-2α, 6β-diyl.

The term "alkyl" (including the alkyl residue of alkoxy and the like) denotes branched or straight alkyl groups of 1 to 18 carbon atoms. The term "alkenyl" (including the alkenyl residue of alkenyloxy and the like) denotes branched or straight alkenyl groups of 2 to 18 carbon atoms.

The term "alkyl in which optionally one >CH—CH< is replaced by >C=C< and/or optionally one methylene group and/or two non-adjacent methylene groups is/are replaced by —O—, —COO— and/or —OOC— and/or optionally a methylene group is replaced by —CHX—" or the term "alkyl or alkyl in which one or more of its carbon atoms are replaced as follows: one >CH—CH< is replaced by >C=C< one methylene group or two non-adjacent methylene groups are replaced by at least one of —O—, —COO—, and —OOC—, or one methylene group is replaced by —CHX—" embraces straight-chain and branched (optionally chiral) residues such as alkyl. 1E-alkenyl, 3E-alkenyl, 4-alkenyl, alkenyl with a terminal double bond, alkoxy, 2E-alkenyloxy, 3-alkenyloxy, alkenyloxy with a terminal double bond, alkoxyalkyl, alkenyloxyalkyl, alkoxycarbonyl, alkoxycarbonylalkoxy, alkanoyloxy, 1-haloalkyl, 2-haloalkyl, 2-haloalkoxy, 2-haloalkoxyCarbonyl, 1-cyanoalkyl, 2-cyanoalkyl, 2-cyanoalkoxy, 2-cyanoalkoxycarbonyl, 1-methylalkyl, 2-methylalkyl, 1-methylalkoxy, 2-methylalkoxy, 2-methylalkoxycarbonyl and the like. Examples of preferred residues are methyl, ethyl, propyl, butyl, pentyl, hexyl, heptyl, octyl, nonyl, decyl, undecyl, dodecyl, 1-methylpropyl, 1-methylheptyl, 2-methylbutyl, 3-methylpentyl, vinyl, 1-E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4Z-heptenyl, 5-hexenyl, 6-heptenyl, 7-octenyl, 8-nonenyl, 9-decenyl, 10-undecenyl, 11-dodecenyl, methoxy, ethoxy, propyloxy, butyloxy, pentyloxy, hexyloxy, heptyloxy, octyloxy, nonyloxy, decyloxy, undecyloxy, dodecyloxy, 1-methylpropyloxy, 1-methylheptyloxy, 2-methylbutyloxy, 3-methylpentyloxy, allyloxy, 2E-butenyloxy, 2E-pentenyloxy, 2E-hexenyloxy, 2E-heptenyloxy, 3-butenyloxy, 3Z-pentenyloxy, 3Z-hexenyloxy, 3Z-heptenyloxy, 4-pentenyloxy, 5-hexenyloxy, 6-heptenyloxy, 7-octenyloxy, 8-nonenyloxy, 9-decenyloxy, 10-undecenyloxy, 11-dodecenyloxy, methoxymethyl, ethoxymethyl, propyloxymethyl, allyloxymethyl, methoxycarbonyl, ethoxycarbonyl, propyloxycarbonyl, 1-methylpropyloxycarbonyl, 1-(methoxycarbonyl)ethoxy, 1-(ethoxycarbonyl)ethoxy, acetoxy, propionyloxy, butyryloxy, 1-fluoropropyl, 1-fluoropentyl, 1-chloropropyl, 2-fluoropropyl, 2-fluoropentyl, 2-chloropropyl, 2-fluoropropyloxy, 2-fluorobutyloxy, 2-fluoropentyloxy, 2-fluorohexyloxy, 2-chloropropyloxy, 2-fluorobutyloxy, 2-fluoropropyloxycarbonyl, 2-fluorobutyloxycarbonyl, 2-fluoropentyloxycarbonyl, 2-fluoro-3-methylbutyloxycarbonyl, 2-fluoro-4-methylpentyloxycarbonyl, 2-chloropropyloxycarbonyl, 1-cyanopropyl, 1-cyanopentyl, 2-cyanopropyl, 2-cyanopentyl, 2-cyanopropyloxy, 2-cyanobutyloxy, 2-cyanopentyloxy, 2-cyanohexyloxy, 2-cyanopropyloxycarbonyl, 2-cyanobutyloxycarbonyl, 2-cyano-3-methylbutyloxycarbonyl, 2-cyano-4-methylpentyloxycarbonyl and the like.

In general, there are preferred those compounds of formula I in which rings $A^1$, $A^2$, $A^3$, $A^4$ and $A^5$ each independently stand for unsubstituted or halogen-, cyano- and/or methyl-substituted 1,4-phenylene or for trans-1,4-cyclohexylene or one of rings $A^1$-$A^5$ (preferably ring $A^2$) also signifies one of the above-mentioned heterocycles and/or one of rings $A^1$-$A^5$ (preferably ring $A^2$) also signifies a ring selected from the group consisting of 1-cyano-trans-1,4-cyclohexylene, bicyclo[2,2,2]octane-1,4-diyl, naphthalene-2,6-diyl, tetralin-2,6-diyl and trans-decalin-2,6-diyl.

A preferred aspect is concerned with the compounds of formula I in which ring $A^3$ represents trans-1,4-cyclohexylene, $Z^2$ signifies a single covalent bond or —CH$_2$CH$_2$— and n stands for the number 0 or 1.

Ring $A^1$ in formula I above preferably stands for unsubstituted or halogen-, cyano- and/or methyl-substituted 1,4-phenylene or, when a low optical anisotropy is desired, also for trans-1,4-cyclohexylene.

A preferred aspect is accordingly concerned with the compounds of the formula

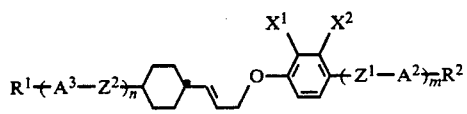  I-1 wherein each of $X^1$ and $X^2$ independently is hydrogen, halogen, cyano or methyl, and $A^2$, $A^3$, $R^1$, $R^2$, $Z^1$, $Z^2$, m and n have the above significances, especially the compounds of the formula

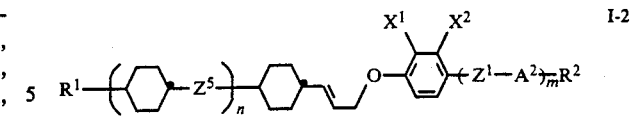  I-2 wherein $Z^5$ is a single covalent bond or —CH$_2$CH$_2$—, each of $X^1$ and $X^2$ independently is hydrogen, halogen, cyano or methyl and $R^1$, $R^2$, $Z^1$, m, n and $A^2$ have the above significances.

A further preferred aspect is concerned with the compounds of the formula

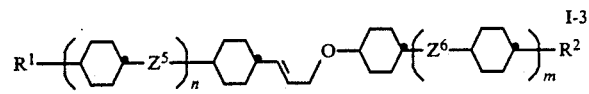  I-3 wherein each of $Z^5$ and $Z^6$ independently is a single covalent bond or —CH$_2$CH$_2$— and $R^1$, $R^2$, m and n have the above significances.

In general there are preferred those compounds of formulae I, I-1, I-2 and I-3 in which $R^1$ is a group $R^3$ and/or $R^2$ is a group $R^4$. There are generally especially preferred the bicyclic compounds ($R^1=R^3$, $R^2=R^4$, m=n=0) and the tricyclic compounds ($R^1=R^3$, $R^2=R^4$ and m=1, n=0 or m=0, n=1).

The compounds with at least 4 rings - i.e. the compounds of formulae I, I-1, I-2 and I-3 in which each of m and n is the integer 1 and/or $R^1$ $^l$ $^{is}$ $^a$ $^{group}$ $^{R3}$—A$^4$—Z$^3$— and/or $R^2$ is a group —Z$^4$—A$^5$—R$^4$ — have, however, distinctly higher clearing points and lower vapour pressure. They are therefore especially suitable as doping substances for increasing the clearing point or as stationary phases in gas chromatography. In this case there are preferred those compounds in which each of $A^4$ and $A^5$ independently is 1,4-phenylene or trans-1,4-cyclohexylene and each of $Z^3$ and $Z^4$ is a single covalent bond, i.e. those compounds of formulae I, I-1, I-2 and I-3 above in which $R^1$ $^{l\ is\ a\ group\ R3}$, 4-$R^3$-phenyl or trans-4-$R^3$-cyclohexyl and $R^2$ is a group $R^4$, 4-$R^4$-phenyl or trans-4-$R^4$-cyclohexyl.

Preferably, each of $Z^1$-$Z^4$ in formula I, I-1, I-2 and I-3 above is a single covalent bond or one of the groups $Z^1$, $Z^2$, $Z^3$ and $Z^4$ also is —COO—, —OOC—, —CH$_2$O—, —OCH$_2$—, —CH$_2$CH$_2$—, —C≡C—, —(CH$_2$)$_3$O—, —O(CH$_2$)$_3$— or the trans configuration of either —CH=CH—CH$_2$O— or —OCH$_2$—CH=CH—.

Further, there are generally preferred those compounds of formulae I, I-1, I-2 and I-3 which have a maximum of 1 or 2 lateral substituents. Preferred lateral substituents are cyano and especially fluorine. Examples of especially preferred sub-groups of compounds of formula I are the compounds of the formulae

  I-4

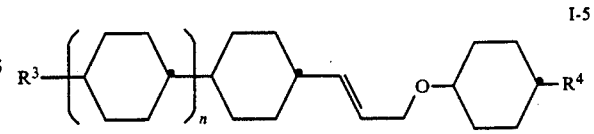  I-5

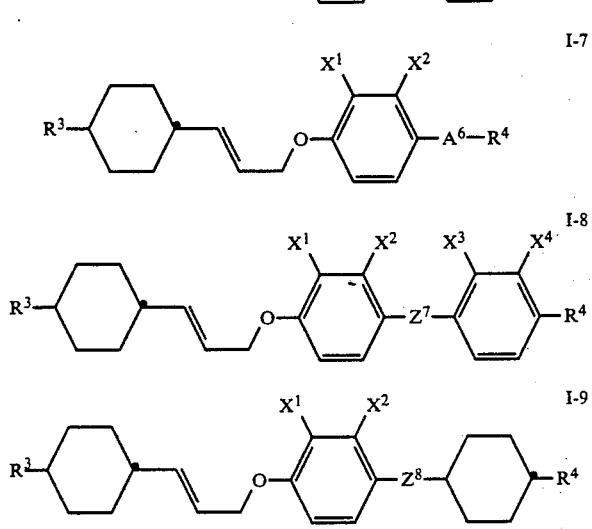

wherein n is the integer 0 or 1; each of $X^1$, $X^2$, $X^3$ and $X^4$ independently is hydrogen, halogen, cyano or methyl; $A^6$ is 1,4-phenylene, pyridine-2,5-diyl, pyrimidine-2,5-diyl, pyrazine-2,5-diyl, trans-1,4-cyclohexylene, trans-1,3-dioxane-2,5-diyl or trans-decalin-2,6-diyl; $Z^7$ is a single covalent bond, —COO— or —OOC—; is a single covalent bond, —OOC—, —OCH$_2$—, —C≡C—, —O(CH$_2$)$_3$— or the trans configuration of —OCH$_2$—CH=CH—; and $R^3$ and $R^4$ have the above significances.

Preferably, $X^1$, $X^2$, $X^3$ and $X^4$ in formulae I-1, I-2, I-4, I-7, I-8 and I-9 above each independently stand for hydrogen, fluorine or cyano, especially for hydrogen or fluorine.

$R^3$ and $R^4$ in formulae I and I-1 to I-9 above preferably have a maximum of in each case about 18 (especially a maximum of in each case about 12) carbon atoms. Further, preferably a maximum of one of the residues $R^3$ $R^4$ signifies halogen, cyano, —NCS, —CF$_3$ or —OCF$_3$. Accordingly, $R^3$ and $R^4$ each independently Preferably signify a C$_1$-C$_{18}$-alkyl or C$_2$-C$_{18}$-alkenyl group in which optionally one methylene group or two non-adjacent methylene groups is/are replaced —COO— and/or —OOC— and/or optionally one methylene group is replaced by —CHX— or one of the residues $R^3$ and can also signify halogen, cyano, —NCS, —CF$_3$ or —OCF$_3$.

For nematic and cholesteric applications there are generally preferred short residues $R^3$ and $R^4$ (e.g. residues with a maximum of 12, preferably a maximum of 7, carbon atoms) and preferably one of the residues can also signify halogen, cyano, —NCS, —CF$_3$ or —OCF$_3$. For smectic applications (especially tilted smectic phases) there are generally preferred those compounds in which each of $R^3$ and $R^4$ independently is alkyl in which optionally one >CH—CH< is replaced by >C=C< and/or optionally one methylene group or two non-adjacent methylene groups is/are replaced by —O—, —COO— and/or —OOC— and/or optionally one methylene group is replaced by —CHX—, and the sum of the carbon atoms in $R^3$ and $R^4$ together amounts to at least 10, preferably at least 12.

Preferred residues $R^3$ are alkyl, alkenyl, alkoxy, alkenyloxy, alkoxycarbonyl, alkenyloxycarbonyl, alkanoyloxy and alkenoyloxy, especially alkyl and alkenyl. In general, residues $R^3$ with up to 12 carbon atoms are especially Preferred. Preferred residues $R^4$ and are alkyl, alkenyl, alkoxy, alkenoyloxy, alkoxycarbonyl, alkenyloxycarbonyl, alkanoyloxy and alkenoyloxy (especially alkyl, alkenyl, alkoxy and alkenyloxy) as well as halogen (especially fluorine and chlorine), cyano, —NCS, —CF$_3$ and —OCF$_3$. In general, residues $R^4$ with up to 12 carbon atoms are especially preferred.

Straight-chain residues $R^3$ and, respectively, $R^4$ are generally preferred. In order to obtain, for example, chiral doping substances for cholesteric liquid crystals or for chiral tilted smectic liquid crystals, one or both residues $R^3$ and $R^4$ can, however, preferably also be branched-chain chiral and/or can have a group —CHX— in which X signifies halogen (preferably fluorine or chlorine), cyano or methyl in place of a methylene group. In order to obtain a high spontaneous polarization for chiral tilted smectic applications, the centre of chirality (i.e. the branching of the chain or the halogen or cyano substituent) should preferably be close to the ring system, for example in the 1- or 2-position of the residue $R^3$ or $R^4$ Further, the tendency to form liquid crystalline phases basically remains when 1 methylene group or 2 non-adjacent methylene groups is/are replaced by —O—, —COO— and/or —OOC—.

The mesophase range, the threshold potential, the response speeds, the steepness of the transmission curves etc. can also be varied by choosing the position of the C=C double bond in unsaturated residues such as alkenyl, alkenyloxy and the like. The effect is fundamentally known from Mol. Cryst. Liq. Cryst. 122, 241 (1985), 131, 109 (1985) and 148, 123 (1987). Residues which have a double bond in the 1-position (especially the E-isomer), in the 3-Position (especially the E-isomer) or in the 4-position (especially the Z-isomer) of the chain including possible hetero atoms, such as 1E-alkenyl, 3E-alkenyl, 4Z-alkenyl, 2E-alkenyloxy, 3Z-alkenyloxy and the like, are preferred. Further, the double bond can preferably also be in the terminal position, especially in the case of compounds for smectic applications. 6-Heptenyl, 7-octenyl, 8-nonenyl, 9-decenyl, 10-undecenyl, 11-dodecenyl, 5-hexenyloxy, 6-heptenyloxy, 7-octenyloxy, 8-nonenyloxY, 9-decenyloxy, 10-undecenyloxy, 11-dodecenyloxy and the like are examples of preferred residues having a double bond in the terminal position.

The compounds of formula I can be manufactured in a manner known per se, for example by etherifying an allyl alcohol of the formula

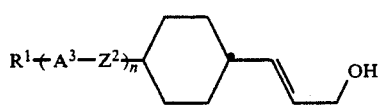

with a compound of the formula

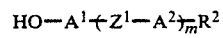

wherein $A^1$, $A^2$, $A^3$, $R^1$, $R^2$, $Z^1$, $Z^2$, m and n have the above significances.

The etherification can preferably be effected in the presence of a dialkyl azodicarboxylate (e.g. diethyl azodicarboxylate) and triphenylphosphine in an inert organic solvent, for example an ether such as tetrahydrofuran, dioxan, diethyl ether and the like. If desired, the compound of formula II can also firstly be converted according to usual methods into a halide (preferably the bromide) and then etherified. The latter method is preferred when $A^1$ represents a saturated ring (especially trans-1,4-cyclohexylene).

If a compound of formula I contains one or more ester groups in $R^1$, $R^2$, $Z^1$ or $Z^2$, then the esterification can be effected preferably after the etherification to the allyl ether. Ether groups which may be present in $R^1$, $R^2$, $Z^1$ or $Z^2$ [i.e. —O— in $R^3$ and $R^4$ and bridging groups —CH$_2$O—, —OCH$_2$—, —(CH$_2$)$_3$O—, —O(CH$_2$)$_3$—, —CH=CH—CH$_2$O— and —OCH$_2$—CH=CH—] or dioxane and dithiane rings can be formed before or after the above etherification to the allyl ether.

The compounds of formula III which have a bridging group —CH=CH—CH$_2$O— or —OCH$_2$—CH=CH— can be prepared in an analogous manner to the methods described below for the compounds of formulae I and II. The remaining compounds of formula III are known compounds or are analogues of known compounds and can be prepared according to known methods.

The compounds of formula II are novel. The manufacture of the compounds of formula I and the preparation of the compounds of formula II is illustrated on the basis of representative examples in Schemes 1–3 in which $A^2$, $A^3$, $R^1$, $R^2$, $R^3$, $R^4$, $X^1$, $X^2$, $X^3$, $X^4$, $Z^1$, $Z^2$, m and have the above significances and $R^5$ denotes alkyl (preferably $C_1$–$C_{10}$-alkyl, particularly $C_1$–$C_5$-alkyl such as methyl, ethyl, Propyl, butyl or pentyl):

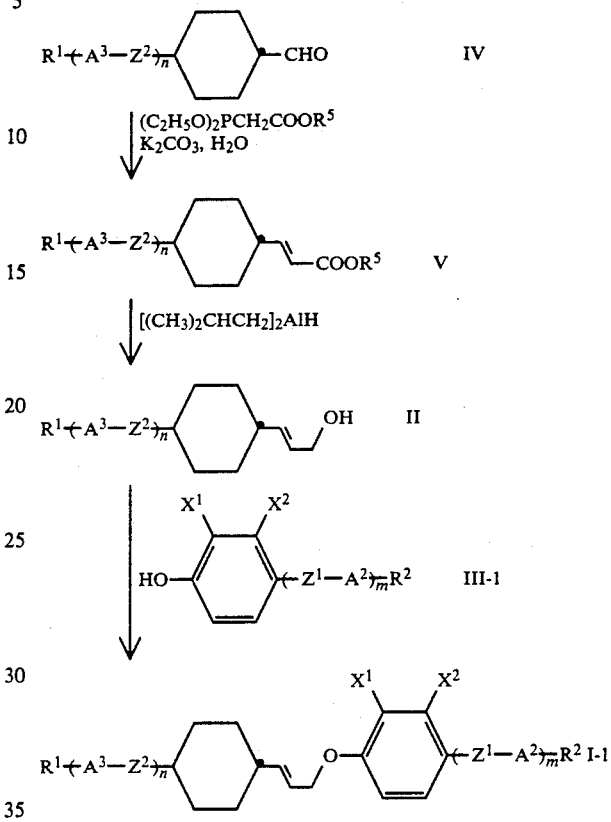

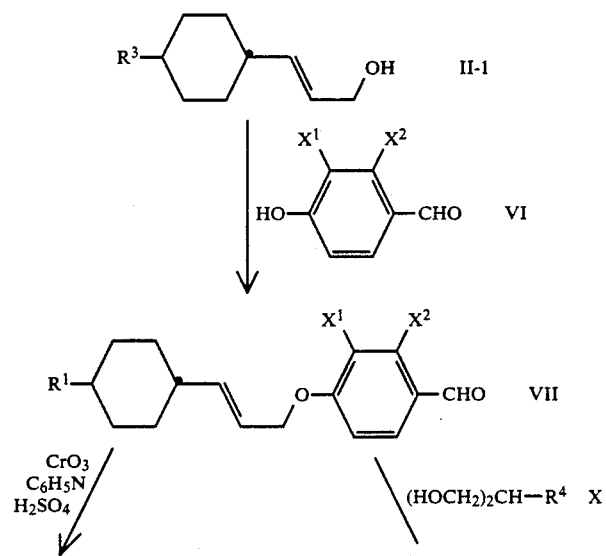

Scheme 2

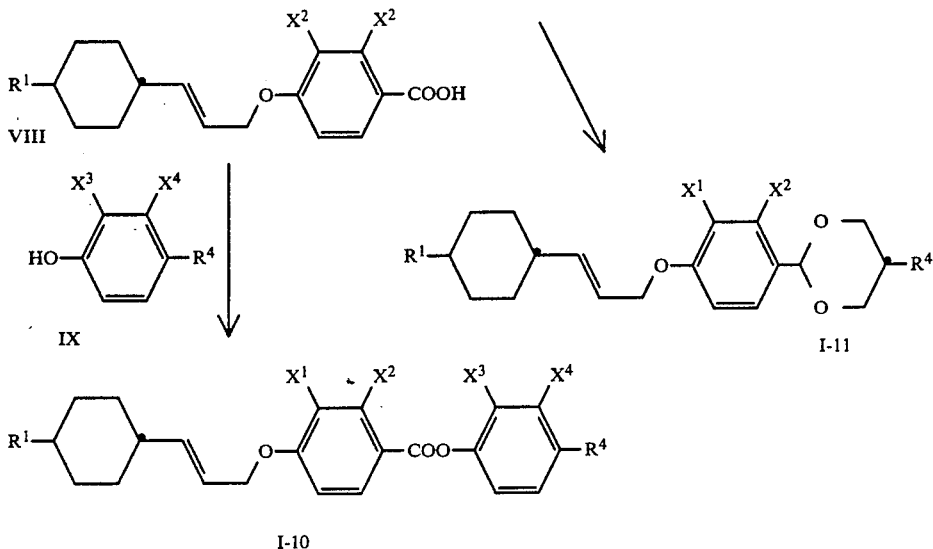

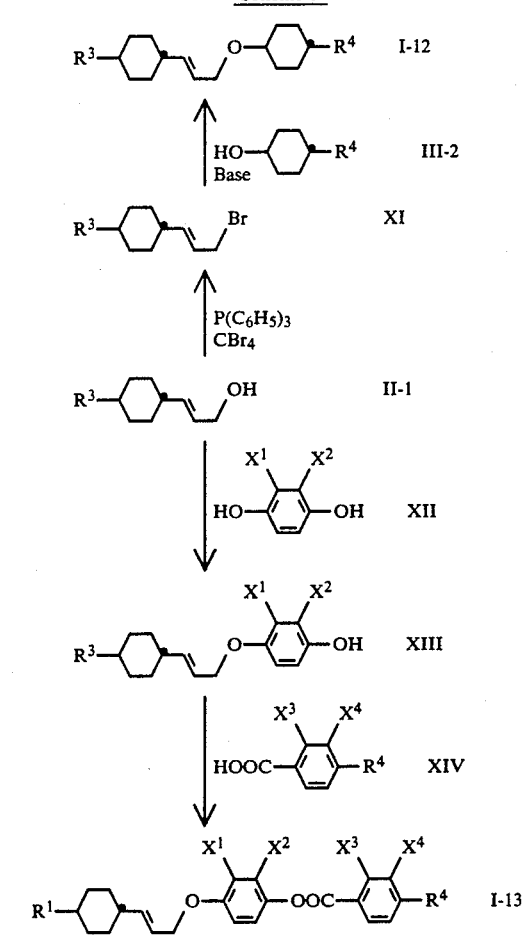

as intermediates for the manufacture of other liquid crystal components.

The above synthesis methods are especially suitable for compounds which have no ester groups in $R^1$, $R^2$, $R^3$, $R^4$, $Z^1$ and $Z^2$. On the other hand, compounds with ester groups can preferably also be obtained by using corresponding compounds which each have in place of the ester group a hydroxy or carboxy group or a group convertible into hydroxy or carboxy and carrying out the conversion into the ester only after the etherification to the allyl ether. Corresponding methods are illustrated in Schemes 2 and 3.

Further, for the manufacture of compounds having a dioxane or dithiane ring, a starting material having a dioxane or dithiane ring can be used or (as illustrated in Scheme 2) the dioxane or dithiane ring can also be formed only after the etherification to the allyl ether.

The conversion of the compound of formula II into the compound of formula I-1 and the conversion of the compound of formula II-1 into the compound of formula VII or XIII can preferably be effected in the presence of a dialkyl azodicarboxylate and triphenylphosphine. If desired, a hydroxy group in the compound of formula XII can be protected by etherification, e.g. to the tetrahydropyranyloxy group.

The esterification of the compound of formula VIII to the compound of formula I-10 or of the compound of formula XIII to the compound of formula I-13 can preferably be effected in the presence of N,N'-dicyclohexylcarbodiimide and 4-(dimethylamino)pyridine.

The etherification of the compound of formula XI can be effected in the presence of usual bases such as lithium hydride, sodium hydride and the like.

The compounds of formula V in which n stands for the number 0 and $R^1$ stands for a group $R^3$ are known from EP-A No. 0107116 or are analogues of these compounds.

The bicyclic and tricyclic compounds of formula V in which n stands for the number 0 or 1 and $R^1$ denotes a group $R^3$—$A^4$—$Z^3$— or n stands for the number 1 and $R^1$ denotes a group $R^3$ are on the other hand novel and are likewise an object of the Present invention. They are also suitable liquid crystal components and for the most part themselves have liquid crystalline properties.

The starting materials used in the Schemes are known compounds or analogues of known compounds and can be prepared according to known methods. In particular, such compounds have already variously been described Compounds of formula V can preferably be obtained directly from the corresponding compounds of formula IV. This also applies to compounds of formula V which contain one or more ester groups in $R^3$, $Z^2$ and/or $Z^3$ when no further conversion into compounds of formula I is desired. In an analogous manner to that which has been stated above, in these cases, however, a compound having a hydroxy or carboxy group or having a group convertible into hydroxy or carboxy can be used as the starting material and the desired ester group can be introduced after conversion into the acrylic acid ester.

Especially preferred bicyclic or tricyclic compounds of formula V are the compounds of the formula

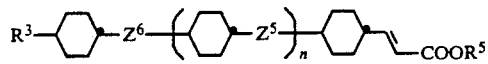   V-1 wherein n is the integer 0 or 1, each of $Z^5$ and $Z^6$ individually is a single covalent bond or —$CH_2CH_2$—, $R^5$ is alkyl and $R^3$ has the above significance.

The compounds of formula V-1 have a very low optical anisotropy and at the same time remarkably broad nematic phases (or in the case of optically active compounds cholesteric phases) with high clearing points.

Preferred residues $R^3$ in formulae V and V-1 are alkyl, alkeny, alkoxy, alkenyloxy, alkoxymethyl, alkenyloxymethyl and 2-(alkoxycarbonyl)vinyl, especially alkyl. These residues preferably have up to 12, especially up to 7, carbon atoms. Straight-chain residues $R^3$ are generally preferred.

$R^5$ in formulae V and V-1 above preferably stands for $C_1$-$C_{10}$-alkyl, especially for $C_1$-$C_5$-alkyl (e.g. ethyl).

Straight-chain residues $R^5$ are generally preferred. Further, one or both of the groups $Z^5$ and $Z^6$ in formula V-1 preferably is a single covalent bond.

The compounds of formulae I and V can be used in the form of mixtures with one another and/or with other liquid crystal components. Suitable liquid crystal components are known in large numbers to the person skilled in the art, e.g. from D. Demus et al., Flüssige Kristalle in Tabellen, VEB Deutscher Verlag für Grundstoffindustrie, Leipzig, Volumes I and II, and, moreover, many of them are commercially available.

The invention is accordingly also concerned with a liquid crystalline mixture having at least 2 components, which is characterized in that at least one component is a compound of formula I (especially one of the compounds referred to as being preferred).

Having regard to the good solubility and, on the other hand, on the large breadth of variation of the properties and fields of application, the amount of compounds of formula I in the mixtures in accordance with the invention can vary in a wide range and can amount to about 0.1 to 100 wt.%. For example, the mixture can consist of compounds of formula I. On the other hand, e.g. chiral 0 doping substances are often used only in relatively small amounts, e.g. about 0.1 to 10 wt.%. In general, however, the amount of compounds of formula I in the mixtures in accordance with the invention amounts to about 1–60 wt.%. As a rule, a range of about 5–30 wt.% is preferred.

The mixtures in accordance with the invention for nematic or cholesteric applications preferably contain, in addition to one or more compounds of formula I, one or more compounds from the group of compounds of the formulae

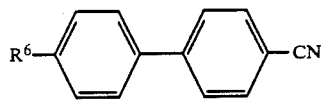   XV

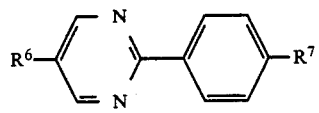   XVI

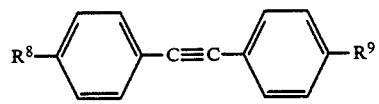   XVII

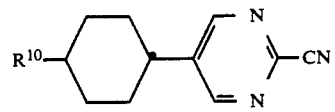   XVIII

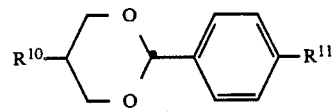   XIX

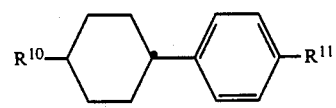   XX

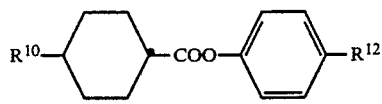 XXI

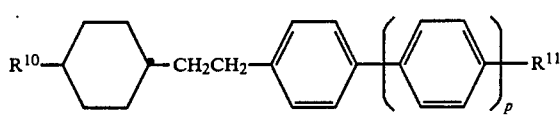 XXII

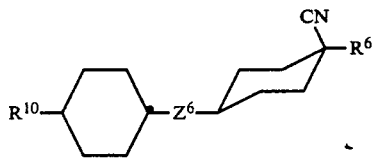 XXIII

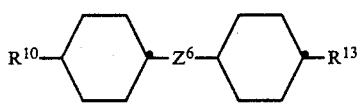 XIV

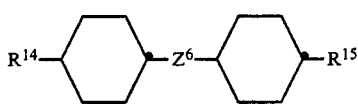 XV

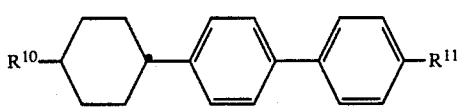 XVI

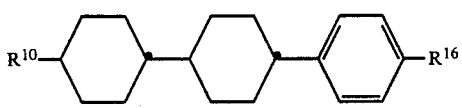 XVII

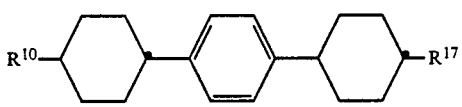 XVIII

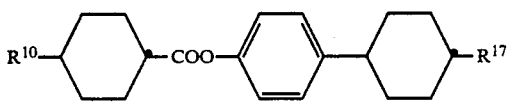 XXIX

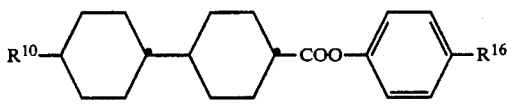 XXX

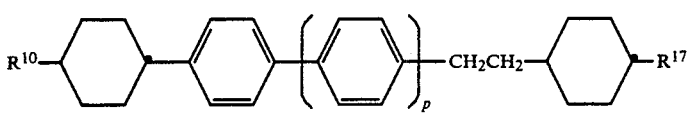 XXXI

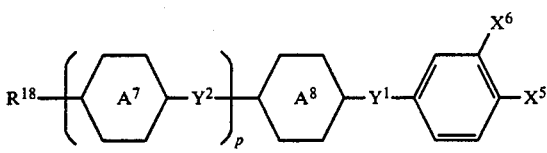 XXXII wherein $R^6$ signifies alkyl, 3E-alkenyl or 4-alkenyl; $R^7$ represents cyano or fluorine; $R^8$ and $R^9$ denote alkyl or alkoxy; and $R^{17}$ each independently signify alkyl, 1E-alkenyl, 3E-alkenyl or 4-alkenyl; $R^{11}$ denotes cyano, —NCS, alkyl, 1E-alkenyl, 3E-alkenyl, 4-alkenyl, alkoxy, 2E-alkenyloxy or 3-alkenyloxy; $R^{12}$ signifies alkoxy, 2E-alkenyloxy or 3-alkenyloxy; p stands for the number 0 or 1; $Z^6$ represents a single covalent bond or —CH$_2$CH$_2$—; $R^{13}$ signifies cyano, alkyl, 1E-alkenyl, 3E-alkenyl or 4-alkenyl; $R^{14}$ denotes alkyl, 1E-alkenyl or 4-alkenyl; $R^{15}$ represents alkoxy, 2E-alkenyloxy or 3-alkenyloxy; $R^{16}$ denotes cyano, alkyl, 1E-alkenyl, 3E-alkenyl, 4-alkenyl, alkoxy, 2E-alkenyloxy or 3-alkenyloxy; $X^5$ denotes fluorine or chlorine and $X^6$ denotes hydrogen, fluorine or chlorine; $R^{18}$ signifies alkyl, 3E-alkenyl, 4-alkenyl, alkoxy, 2E-alkenyloxy or 3-alkenyloxy; one of the groups $Y^1$ and $Y^2$ signifies a single covalent bond, —COO—, —OOC—, —CH$_2$CH$_2$—, —CH$_2$O— or —OCH$_2$— and the other of the groups $Y^1$ and $Y^2$ signifies a single covalent bond; and rings $A^7$ and $A^8$ each independently represent trans-1,4-cyclohexylene in which optionally 2 non-adjacent CH$_2$ groups are replaced by oxygen or 1,4-phenylene in which optionally 1 CH group or 2 CH groups is/are replaced by nitrogen.

Preferably, the residues $R^6$ and $R^8$–$R^{18}$ have a maximum of in each case 12 carbon atoms, especially a maximum of in each case 7 carbon atoms.

The mixtures in accordance with the invention for smectic applications (especially for tilted smectic or chiral tilted smectic phases) preferably contain, in addition to one or more compounds of formula I, one or more compounds from the group of compounds of the formulae atoms; r and s each independently signify 1 or 2; $R^{21}$ and $R^{22}$ denote alkyl, alkoxy or alkenyloxy with up to 18 carbon atoms; ring B represents unsubstituted or halogen- and/or methyl-substituted 1,4-phenylene; ring C represents trans-1,4-cyclohexylene or unsubstituted or halogen- and/or methyl-substituted 1,4-phenylene; p and q each independently stand for the number 0 or 1; $R^{23}$ and each independently signify an unsubstituted or halogen-substituted $C_1$–$C_{18}$-alkyl or $C_2$–$C_{18}$-alkenyl group in which optionally one CH$_2$ group or two non-adjacent CH$_2$ groups is/are replaced by —O—, —COO— and/or —OOC—; rings $D^1$, $D^2$ and $D^3$ each independently represent unsubstituted or cyano-, halogen- or lower alkyl-substituted 1,4-phenylene; $Z^9$ denotes a single covalent bond, —CH$_2$CH$_2$—, —OCH$_2$—, —COO— or —OOC—; and $R^{26}$ each independently signify an unsubstituted or halogen-substituted $C_1$–$C_{18}$-alkyl or $C_2$–$C_{18}$-alkenyl group in which optionally one CH$_2$ group or two non-adjacent CH$_2$ groups is/are replaced by oxygen; ring $D^4$ represents trans-1,4-cyclohexylene or unsubstituted or cyano-, halogen- or lower alkyl-substituted 1,4-phenylene; $Z^{10}$, $Z^{11}$ and each independently signify a single covalent bond, —COO—, —OOC—, —CH$_2$CH$_2$—, —OCH$_2$— or

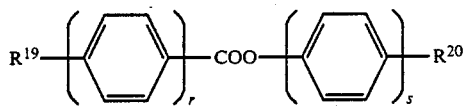

XXXIII

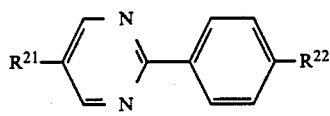

XXXIV

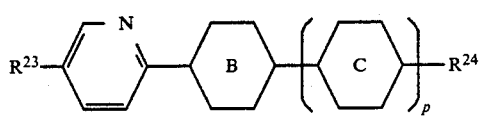

XXXV

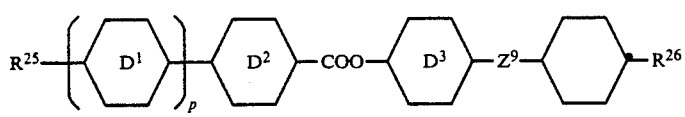

XXXVI

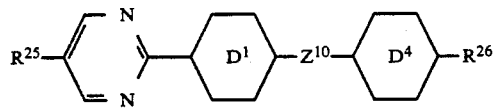

XXXV

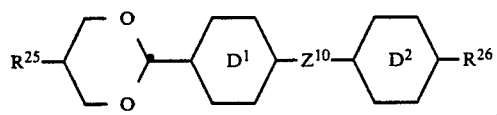

XXXVI

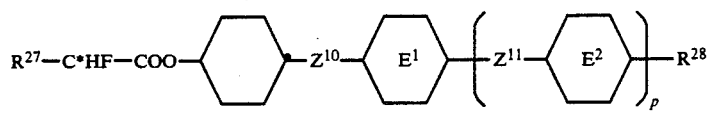

XXXVII

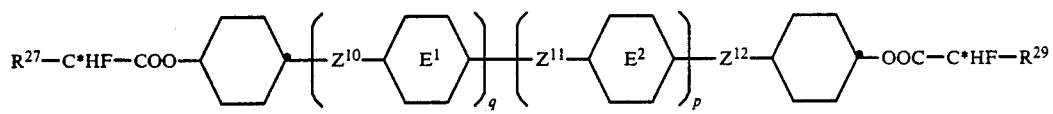

XXXVIII wherein $R^{19}$ and $R^{20}$ denote alkyl, alkoxy, alkenyloxy, alkanoyloxy or alkoxycarbonyl with up to 18 carbon —CH$_2$O—; $R^{27}$ and $R^{29}$ each independently signify a $C_1$–$C_{15}$-alkyl or $C_2$–$C_{15}$-alkenyl group in which optionally one $CH_2$ group is replaced by oxygen; $R^{28}$ denotes an unsubstituted or halogen-substituted $C_1$–$C_{15}$-alkyl or $C_2$–$C_{15}$-alkenyl group in which optionally one $CH_2$ group is replaced by oxygen and/or optionally one $CH_2$ group is replaced by an ester group —COO— or —OOC—; rings $E^1$ and $E^2$ each independently represent unsubstituted or halogen-, cyano- and/or methyl-substituted 1,4-phenylene in which optionally 1 CH group or 2 CH groups is/are replaced by nitrogen; and C* denotes a chiral carbon atom.

The invention is also concerned with a liquid crystalline mixture having at least 2 components, wherein at least one component is a compound of formula V in which n is the integer 0 or 1 and $R^{1\ l\ is\ a\ group\ R3}$—A$^4$—Z$^3$— or n is the integer 1 and $R^{1\ l\ is\ R3}$. Preferred mixtures are those which contain one or more of the compounds of formula V which are referred to as being preferred.

The amount of compounds of formula V in the mixture can vary in a wide range and can amount, for example, to about 1–50 wt.%. In general, a range of about 5–30 wt.% is preferred.

The bicyclic and tricyclic compounds of formula V are preferably used as components of nematic or cholesteric mixtures. The mixtures Preferably contain, in addition to one or more bicyclic or tricyclic compounds of formula V, one or more compounds from the group of compounds of formulae I and XV–XXXII above.

The manufacture of the liquid crystalline mixtures and of the electro-optical devices can be effected in a manner known per se.

The invention is illustrated further by the following Examples. The optical antipodes of chiral compounds have in each case the same phase transition temperatures and absolutely the same values of the twisting, but with opposite signs. Room temperature is about 20° C. The abbreviations used for the characterization of the phase transitions have the following significances:

---
C stands for crystalline
S stands for smectic
$S_A$, $S_B$, $S_C$ etc. stand for smectic A, B, C etc.
$S_C^*$, $S_F^*$ etc. stand for chiral smectic C, F etc.
N stands for nematic
N* stands for cholesteric
I stands for isotropic.
---

Unless otherwise indicated, the examples were carried out as written.

EXAMPLE 1

A mixture of 0.5 g of (E)-3-(trans-4-pentylcyclohexyl)allyl alcohol, 0.3 g of 4-methoxyphenol, 0.4 g of diethyl azodicarboxylate, 0.6 g of triphenylphosphine and 25 ml of absolute tetrahydrofuran was stirred at room temperature overnight and then concentrated. The residue was suspended with 50 ml of hot hexane and filtered. The filtrate was concentrated. Chromatography of the residue on silica gel with toluene/hexane (vol. 1:1) and recrystallization from methanol gave pure 4-methoxyphenyl (E)-3-(trans-4-pentylcyclohexyl)allyl ether with m.p. (C-N) 45° C. and cl.p. (N-I) 46° C.

The (E)-3-(trans-4-pentylcyclohexyl)allyl alcohol used as the starting material was prepared as follows:

a) A mixture of 10 g of trans-4-pentylcyclohexanecarboxaldehyde and 16 g of ethyl diethylphosphonoacetate $(C_2H_5O)_2PCH_2COOC_2H_5$ was treated dropwise at room temperature with a solution of 15 g of potassium carbonate in 11 ml of water. The reaction mixture was stirred at room temperature overnight and then poured into 500 ml of water and extracted four times with 50 ml of hexane each time. The combined organic phases were washed twice with 500 ml of water each time, dried over magnesium sulphate, filtered and concentrated. Chromatography of the residue on silica gel with toluene finally gave 13.5 g of ethyl (E)-3-(trans-4-pentylcyclohexyl)acrylate with b.p. 114–116° C./0.07 mmHg.

b) A solution of 13.5 g of ethyl (E)-3-(trans-4-pentylcyclohexyl)acrylate in 100 ml of dichloromethane was treated dropwise at −78° C. and while gassing with nitrogen with 100 ml of a 20% solution of diisobutylaluminium hydride in hexane. After completion of the addition the slightly yellow solution was stirred for a further 1 hour and then treated cautiously with 10 ml of 25% hydrochloric acid. The reaction mixture was poured into 100 ml of water and the organic phase was separated. The aqueous phase was back-extracted twice with 100 ml of dichloromethane each time. The combined organic phases were washed with 500 ml of water, 500 ml of concentrated potassium hydrogen carbonate solution and again with 500 ml of water and subsequently dried over magnesium sulphate, filtered and concentrated. Distillation of the residue gave 10 g of (E)-3-(trans-4-pentylcyclohexyl)allyl alcohol with b.p. 174–175° C./15 mmHg.

The following compounds can be manufactured in an analogous manner. Those compounds shown with accompanying data actually were made.

4-ethoxyphenyl (E)-3-(trans-4-pentylcyclohexyl)allyl ether, m.p. (C-I) 62° C., cl.P. (N-I) 59° C.;

4-propyloxyphenyl (E)-3-(trans-4-pentylcyclohexyl)allyl ether, m.p. (C-I) 72° C., cl.p. (N-I) 50° C.;

4-butyloxyphenyl (E)-3-(trans-4-pentylcyclohexyl)allyl ether, m.p. (C-I) 59° C., $S_A$-N 43° C., cl.p. (N-I) 61° C.;

4-pentyloxyphenyl (E)-3-(trans-4-pentylcyclohexyl)allyl ether, m.p. (C-$S_A$) 41° C., $S_A$-N 46° C., cl.p. (N-I) 54° C.;

4-hexyloxyphenyl (E)-3-(trans-4-pentylcyclohexyl)allyl ether, m.p. (C-$S_A$) 50° C., $S_A$-N 55° C., cl.p. (N-I) 60° C.;

4-heptyloxyphenyl (E)-3-(trans-4-pentylcyclohexyl)allyl ether, m.p. (C-$S_A$) 42° C., $S_A$-N 57° C., cl.p. (N-I) 58° C.;

4-octyloxyphenyl (E)-3-(trans-4-pentylcyclohexyl)allyl ether;

4-nonyloxyphenyl (E)-3-(trans-4-pentylcyclohexyl)allyl ether;

4-decyloxyphenyl (E)-3-(trans-4-pentylcyclohexyl)allyl ether;

4-cyanophenyl (E)-3-(trans-4-methylcyclohexyl)allyl ether;

4-cyanophenyl (E)-3-(trans-4-ethylcyclohexyl)allyl ether;

4-cyanophenyl (E)-3-(trans-4-propylcyclohexyl)ally ether;

4-cyanophenyl (E)-3-(trans-4-butylcyclohexyl)allyl ether;

4-cyanophenyl (E)-3-(trans-4-pentylcyclohexyl)allyl ether, m.p. (C-I) 64° C., cl.p. (N-I) 43° C.;

4-cyanophenyl (E)-3-(trans-4-hexylcyclohexyl)allyl ether;

4-cyanophenyl (E)-3-(trans-4-heptylcyclohexyl)allyl ether;

4-cyanophenyl (E)-3-(trans-4-octylcyclohexyl)allyl ether;
4-fluorophenyl (E)-3-(trans-4-propylcyclohexyl)allyl ether;
4-fluorophenyl (E)-3-(trans-4-pentylcyclohexyl)allyl ether, m.p. (C-I) 23° C.;
3,4-difluorophenyl (E)-3-(trans-4-propylcyclohexyl)allyl ether;
3,4-difluorophenyl (E)-3-(trans-4-pentylcyclohexyl)allyl ether, m.p. (C-I) 11° C.;
2,3-difluoro-4-methoxyphenyl (E)-3-(trans-4-pentylcyclohexyl)allyl ether;
2,3-difluoro-4-ethoxyphenyl (E)-3-(trans-4-Pentylcyclohexyl)allyl ether, m.p. (C-I) 23° C., cl.P. (N-I) 5° C.;
2,3-difluoro-4-propyloxyphenyl (E)-3-(trans-4-pentylcyclohexyl)allyl ether;
2,3-difluoro-4-butyloxyphenyl (E)-3-(trans-4-pentylcyclohexyl)allyl ether;
4-chlorophenyl (E)-3-(trans-4-pentylcyclohexyl)allyl ether, m.p. (C-I) 55° C.;
4-bromophenyl (E)-3-(trans-4-pentylcyclohexyl)allyl ether, m.p. (C-I) 65° C.;
4-iodophenyl (E)-3-(trans-4-pentylcyclohexyl)allyl ether, m.p. (C-I) 66° C.;
2,3-dicyano-4-pentylphenyl (E)-3-(trans-4-propylcyclohexyl)allyl ether;
2,3-dicyano-4-pentylphenyl (E)-3-(trans-4-pentylcyclohexyl)allyl ether;
2,3dicyano-4-pentylphenyl (E)-3-(trans-4-heptylcyclohexyl)allyl ether;
2-fluoro-4-cyanophenyl (E)-3-(trans-4-propylcyclohexyl)allyl ether;
2-fluoro-4-cyanophenyl (E)-3-(trans-4-pentylcyclohexyl)allyl ether;
2-fluoro-4-cyanophenyl (E)-3-(trans-4-heptylcyclohexyl)allyl ether;
3-fluoro-4-cyanophenyl (E)-3-(trans-4-propylcyclohexyl)allyl ether;
3-fluoro-4-cyanophenyl (E)-3-(trans-4-pentylcyclohexyl)allyl ether, m.p. (C-I) 51° C.;
4-(trans-4-propylcyclohexyl)phenyl (E)-3-(trans-4-propylcyclohexyl)allyl ether;
4-(trans-4-pentylcyclohexyl)phenyl (E)-3-(trans-4-propylcyclohexyl)allyl ether;
4-(trans-4-heptylcyclohexyl)phenyl (E)-3-(trans-4-propylcyclohexyl)allyl ether;
4-(trans-4-propylcyclohexyl)phenyl (E)-3-(trans-4-pentylcyclohexyl)allyl ether;
4-(trans-4-pentylcyclohexyl)phenyl (E)-3-(trans-4-pentylcyclohexyl)allyl ether, m.p. (C-SB) 56° C., $S_B$-$S_A$ 109° C., $S_A$-N 113° C., cl.P. (N-I) 136° C.;
4-(trans-4-heptylcyclohexyl)phenyl (E)-3-(trans-4-pentylcyclohexyl)allyl ether;
4-(trans-4-propylcyclohexyl)phenyl (E)-3-(trans-4-heptylcyclohexyl)allyl ether;
4-(trans-4-pentylcyclohexyl)phenyl (E)-3-(trans-4-heptylcyclohexyl)allyl ether;
4-(trans-4-heptylcyclohexyl)phenyl (E)-3-(trans-4-heptylcyclohexyl)allyl ether;
4-propylcyclohexyl)ethyl]phenyl (E)-3-(trans-4-propylcyclohexyl)allyl ether;
4-[2-(trans-4-pentylcyclohexyl)ethyl]phenyl (E)-3-(trans-4-propylcyclohexyl)allyl ether;
4-[2-(trans-4-heptylcyclohexyl)ethyl]phenyl (E)-3-(trans-4-propylcyclohexyl)allyl ether;
4-[2-(trans-4-propylcyclohexyl)ethyl]phenyl (E)-3-(trans-4-entylcyclohexyl)allyl ether;
4-[2-(trans-4-pentylcyclohexyl)ethyl]phenyl (E)-3-(trans-4-pentylcyclohexyl)allyl ether, m.p. (C-SB) 8° C., $S_B$-$S_A$ 103° C., $S_A$-N 110° C., cl.p. (N-I) 123° C.;
4-[2-(trans-4-heptylcyclohexyl)ethyl]phenyl (E)-3-(trans-4-pentylcyclohexyl)allyl ether;
4-[2-(trans-4-propylcyclohexyl)ethyl]phenyl (E)-3-(trans-4-heptylcyclohexyl)allyl ether;
4-[2-(trans-4-pentylcyclohexyl)ethyl]phenyl (E)-3-(trans-4-heptylcyclohexyl)allyl ether;
4-[2-(trans-4-heptylcyclohexyl)ethyl]phenyl (E)-3-(trans-4-heptylcyclohexyl)allyl ether;
4-[(trans-4-propylcyclohexyl)methoxy]phenyl (E)-3-(trans-4-pentylcyclohexyl)allyl ether;
4-[(trans-4-pentylcyclohexyl)methoxy]phenyl (E)-3-(trans-4-pentylcyclohexyl)allyl ether, m.p. (C-$S_B$) 84° C., $S_b$-$S_1$ 101° C., cl.p. ($S_A$-I) 116° C.;
4-[3-(trans-4-propylcyclohexyl)-1-propyloxy (E)-3-(trans-4-pentylcyclohexyl)allyl ether;
4-[3-(trans-4-pentylcyclohexyl)-1-propyloxy (E)-3-(trans-4-pentylcyclohexyl)allyl ether, m.p. (C-$S_A$) 115° C., $S_A$-N 116° C., cl.P. (N-I) 120° C.;
4-[3-(trans-4-heptylcyclohexyl)-1-propyloxy (E)-3-(trans-4-pentylcyclohexyl)allyl ether;
4'-(trans-4-propylcyclohexyl)-4-biphenylyl (E)-3-(trans-4-propylcyclohexyl)allyl ether;
4'-(trans-4-propylcyclohexyl)-4-biphenylyl (E)-3-(trans-4-pentylcyclohexyl)allyl ether;
4'-(trans-4-pentylcyclohexyl)-4-biphenylyl (E)-3-(trans-4-propylcyclohexyl)allyl ether;
4'-(trans-4-pentylcyclohexyl)-4-biphenylyl (E)-3-(trans-4-pentylcyclohexyl)allyl ether;
4'-cyano-4-biphenylyl (E)-3-(trans-4-propylcyclohexyl)allyl ether;
4'-cyano-4-biphenylyl (E)-3-(trans-4-pentylcyclo l)allyl ether;
4'-cyano-4-biphenylyl (E)-3-(trans-4-heptylcyclohexyl)allyl ether;
4'-fluoro-4-biphenylyl (E)-3-(trans-4-propylcyclohexyl)allyl ether;
4'-fluoro-4-biphenylyl (E)-3-(trans-4-pentylcyclohexyl)allyl ether;
4'-fluoro-4-biphenylyl (E)-3-(trans-4-heptylcyclohexyl)allyl ether;
3',4'-difluoro-4-biphenylyl (E)-3-(trans-4-propylcyclohexyl)allyl ether;
3',4'-difluoro-4-biphenylyl (E)-3-(trans-4-pentylcyclohexyl)allyl ether;
3',4'-difluoro-4-biphenylyl (E)-3-(trans-4-heptylcyclohexyl)allyl ether;
ethyl (R)-2-(4'-[(E)-3-(trans-4-Pentylcyclohexyl)allyloxy]-4-biphenylyloxy)propionate, m.p. (C-Ch) 77° C., $S_A$-Ch 76° C., cl.P. (Ch-I) 83° C.;
5-pentyl-2-(4-[(E)-3-(trans-4-Pentylcyclohexyl)allyloxy]phenyl)pyrimidine, m.p. (C-N) 77° C., cl.p. (N-I) 144° C.;
5-hexyl-2-(4-[(E)-3-(trans-4-pentylcyclohexyl)-allyloxy]phenyl)pyrimidine, m.p. (C-N) 83° C., cl.p (N-I) 139° C.;
5-heptyl-2-(4-[(E)-3-(trans-4-pentylcyclohexyl)allyloxy]phenyl)pyrimidine, m.p. (C-N) 91° C., cl.p. (N-I) 141° C.;
5-octyl-2-(4-[(E)-3-(trans-4-pentylcyclohexyl)allyloxy]-phenyl)pyrimidine, m.p. (C-SC) 87° C., SC-N 88° C., cl.P. (N-I) 138° C.;
5-nonyl-2-(4-[(E)-3-(trans-4-pentylcyclohexyl)allyloxy]phenyl)pyrimidine, m.p. (C-SC) 79° C., SC-N 102° C., cl.p. (N-I) 138° C.;

5-decyl-2-(4-[(E)-3-(trans-4-pentylcyclohexyl)allyloxy]-phenyl)pyrimidine;

5-octyl-2-(4-[(E)-3-(trans-4-pentylcyclohexyl)allyloxy]-phenyl)pyridine;

5-nonyl-2-(4-[(E)-3-(trans-4-pentylcyclohexyl)allyloxy]phenyl)pyridine;

5-decyl-2-(4-[(E)-3-(trans-4-pentylcyclohexyl)allyloxy]-phenyl)pyridine, m.p. (C-S) -35° C., S-S 128° C., S-$S_C$ 130° C., cl.P. (SC-I) 145° C.;

3,4-difluorophenyl (E)-3-[trans-4-(trans-4-propylcyclohexyl)cyclohexyl]allyl ether, m.p. (C-N) 48° C., cl.p. (N-I) 101° C.;

3,4-difluorophenyl (E)-3-[trans-4-(trans-4-butylcyclohexyl)cyclohexyl]allyl ether;

3,4-difluorophenyl (E)-3-[trans-4-(trans-4-pentylcyclohexyl)cyclohexyl]allyl ether, m.p. (C-N) 52° C., cl.p. (N-I) 103° C.;

4-fluorophenyl (E)-3-[trans-4-(trans-4-propylcyclohexyl)cyclohexyl]allyl ether, m.p. (C-N) 75° C., cl.p. (N-I) 127° C.;

4-fluorophenyl (E)-3-[trans-4-(trans-4-butylcyclohexyl)cyclohexyl]allyl ether;

4-fluorophenyl (E)-3-[trans-4-(trans-4-pentylcyclohexyl)cyclohexyl]allyl ether, m.p (C-N) 68° C., $S_B$-N 60° C., cl.p. (N-I) 131° C.;

4-cyano-2-fluorophenyl (E)-3-trans-4-(trans-3-propylcyclohexyl)cyclohexyl]allyl ether;

4-cyano-2-fluorophenyl (E)-3-[trans-4-(trans-3-pentylcyclohexyl)cyclohexyl]allyl ether;

4-cyano-2-fluorophenyl (E)-3-[trans-4-(trans-3-pentylcyclohexyl)cyclohexyl]allyl ether;

4-cyano-2-fluorophenyl (E)-3-[trans-4-(trans-3-heptylcyclohexyl)cyclohexyl]allyl ether;

4-cyano-3-fluorophenyl (E)-3-[trans-4-(trans-3-propylcyclohexyl)cyclohexyl]allyl ether, m.p. (C-N) 93° C., cl.p. (N-I) 138° C.;

4-cyano-3-fluorophenyl (E)-3-[trans-4-(trans-3-pentylcyclohexyl)cyclohexyl]allyl ether, m.p. (C-N) 99° C., cl.p. (N-I) 141° C.;

4-cyanophenyl (E)-3-[trans-4-(trans-4-propylcyclohexyl)cyclohexyl]allyl ether, m.p. (C-N) 96° C., cl.p. (N-I) 66° C.;

4-cyanophenyl (E)-3-[trans-4-(trans-4-pentylcyclohexyl)cyclohexyl]allyl ether, m.p. (C-N) 102° C., cl.p. (N-I) 165° C.;

2,3-difluoro-4-methoxyphenyl (E)-3-[trans-4-(trans-4-trans-propylcyclohexyl)cyclohexyl]allyl ether;

2,3-difluoro-4-ethoxyphenyl (E)-3-[trans-4-(trans-4-propylcyclohexyl)cyclohexyl]allyl ether, m.p. (C-N) 65° C., cl P. (N-I) 136° C.;

2,3-difluoro-4-propyloxyphenyl (E)-3-[trans-4-(trans-4-Propylcyclohexyl)cyclohexyl]allyl ether;

2,3-difluoro-4-butyloxyphenyl (E)-3-[trans-4-(trans-4-propylcyclohexyl)cyclohexyl]allyl ether, m.p. (C-N) 54° C., cl.p. (N-I) 127° C.;

2,3-difluoro-4-pentyloxyphenyl (E)-3-[trans-4-(trans-4-propylcyclohexyl)cyclohexyl]allyl ether;

2,3-difluoro-4-methoxyphenyl (E)-3-[trans-4-(trans-4-pentylcyclohexyl)cyclohexyl]allyl ether;

2,3-difluoro-4-ethoxyphenyl (E)-3-[trans-4-(trans-4-pentylcyclohexyl)cyclohexyl]allyl ether, m.p. (C-N) 51° C., cl.p. (N-I) 140° C.;

2,3-difluoro-4-propyloxyphenyl (E)-3-[trans-4-(trans-4-pentylcyclohexyl)cyclohexyl]allyl ether;

2,3-difluoro-4-butyloxyphenyl (E)-3-[trans-4-(trans-4-pentylcyclohexyl)cyclohexyl]allyl ether;

2,3-difluoro-4-pentyloxyphenyl (E)-3-[trans-4-(trans-4-pentylcyclohexyl)cyclohexyl]allyl ether;

2,3-dicyano-4-pentylphenyl (E)-3-[trans-4-(trans-4-propylcyclohexyl)cyclohexyl]allyl ether;

2,3-dicyano-4-pentylphenyl (E)-3-[trans-4-(trans-4-pentylcyclohexyl)cyclohexyl]allyl ether;

2,3-dicyano-4-pentylphenyl (E)-3-[trans-4-(trans-4-heptylcyclohexyl)cyclohexyl]allyl ether; 4-(trans-4-propylCyClohexyl)phenyl (E)-3-[trans-4-(trans-4-propylcyclohexyl)cyclohexyl]allyl ether; 4-(trans-4-propylcyclohexyl (E)-3-[trans-4-(trans-4-pentylcyclohexyl)cyclohexyl]allyl ether;

4-pentylcyclohexyl)phenyl (E)-3-[trans-4-(trans-4-propylcyclohexyl)cyclohexyl]allyl ether;

4-(trans-4-pentylcyclohexyl)phenyl (E)-3-[trans-4-(trans-4-pentylcyclohexyl)cyclohexyl]allyl ether;

4-[(4a$\beta$H,8a$\beta$H)-decahydro-6$\beta$-pentyl-2$\alpha$-naphthyl]-phenyl (E)-3-(trans-4-pentylcyclohexyl)allyl ether, m.p. (C-$S_A$) 96° C., $S_A$-N 127° C., cl.P. (N-I) 172° C..

EXAMPLE 2

2.0 g of 2,3-difluoro-4-dodecyloxybenzoic acid, 1.8 g of 4-[(E)-3-(trans-4-pentylcyclohexyl)allyloxy]phenol and 0.1 g of 4-(dimethylamino)pyridine were dissolved in 50 ml of dichloromethane and the solution was treated portionwise within 10 minutes while stirring with 1.4 g of N,N'-dicyclohexylcarbodiimide. The mixture was stirred at room temperature overnight and then filtered. The filtrate was diluted with dichloromethane, washed twice with 50 ml of saturated sodium carbonate solution each time and then with water, dried over magnesium sulphate and concentrated. The crude product obtained was purified by chromatography on silica gel with toluene. The 2,3-difluoro-4-dodecyloxybenzoic acid 4-[(E)-3-(trans-4-pentylcyclohexyl)allyloxy]phenyl ester obtained was recrystallized from ethanol; m.p. (C-$S_C$) 73° C., $S_C$-N 124° C., cl.p. (N-I) 137° C..

The 4-[(E)-3-(trans-4-pentylcyclohexyl)allylOxy]-phenol used as the starting material was prepared as follows:

10 g of (E)-3-(trans-4-pentylcyclohexyl)allyl alcohol, 26 g of hydroquinone, 8 g of diethyl azodicarboxylate, 12 g of triphenylphosphine and 500 ml of tetrahydrofuran were reacted in an analogous manner to Example 1. This gave 16 g of 4-[(E)-3-(trans-4-pentylcyclohexyl)allyloxy]henol, m.p. 97-98° C..

The following compounds can be manufactured in an analogous manner. Those compounds shown with accompanying data actually were made.

2,3-Difluoro-4-heptyloxybenzoic acid 4-[(E)-3-(trans-4-pentylcyclohexyl)allyloxy]phenyl ester, m.p. (C-$S_C$) 66° C., $S_C$-N 95° C., cl.p. (N-I) 144° C.;

2,3-difluoro-4-octyloxybenzoic acid 4-[(E)-3-(trans-4-pentylcyclohexyl)allyloxy]phenyl ester, m.p. (C-$S_C$) 76° C., $S_C$-N 106° C., cl.p. (N-I) 143° C.;

2,3-difluoro-4-nonyloxybenzoic acid 4-[(E)-3-(trans-4-pentylcyclohexyl)allyloxy]phenyl ester, m.p. (C-$S_C$) 74° C., $S_C$-N 114° C., cl.p. (N-I) 141° C.;

2,3-difluoro-4-decyloxybenzoic acid 4-[(E)-3-(trans-4-pentylcyclohexyl)allyloxy]phenyl ester, m.p. (C-$S_C$) 80° C., $S_C$-N 119° C., cl.p. (N-I) 140° C.;

2,3-difluoro-4-undecyloxybenzoic acid 4-[(E)-3-(trans-4-pentylcyclohexyl)allyloxy]phenyl ester, m.p. (C-$S_C$) 77° C., $S_C$-N 121° C., cl.p. (N-I) 137° C.;

4-methoxybenzoic acid 4-[(E)-3-(trans-4-pentylcyclohexyl)allyloxy]phenyl ester;

4-ethoxybenzoic acid 4-[(E)-3-(trans-4-pentylcyclohexyl)allyloxy]phenyl ester;

4-propyloxybenzoic acid 4-[(E)-3-(trans-4-pentylcyclohexyl)allyloxy]phenyl ester;
4-butyloxybenzoic acid-4-[(E)-3-(trans-4-pentylcyclohexyl)allyloxy]phenyl ester;
4-pentyloxybenzoic acid 4-[(E)-3-(trans-4-pentylcyclohexyl)allyloxy]phenyl ester;
4-hexyloxybenzoic acid 4-[(E)-3-(trans-4-pentylcyclohexyl)allyloxy]phenyl ester;
4-heptyloxybenzoic acid 4-[(E)-3-(trans-4-pentylcyclohexyl)allyloxy]phenyl ester;
4-octyloxybenzoic acid 4-[(E)-3-(trans-4-pentylcyclohexyl)allyloxy]phenyl ester;
4-nonyloxybenzoic acid 4-[(E)-3-(trans-4-pentylcyclohexyl)allyloxy]phenyl ester;
4-decyloxybenzoic acid 4-[(E)-3-(trans-4-pentylcyclohexyl)allyloxy]phenyl ester;
trans-4-methylcyclohexanecarboxylic acid 4-[(E)-3-(trans-4-pentylcyclohexyl)allyloxy]phenyl ester;
trans-4-ethylcyclohexanecarboxylic acid 4-[(E)-3-(trans-4-pentylcyclohexyl)allyloxy]phenyl ester;
trans-4-propylcyclohexanecarboxylic acid 4-[(E)-3-(trans-4-pentylcyclohexyl)allyloxy]phenyl ester;
trans-4-butylcyclohexanecarboxylic acid 4-[(E)-3-(trans-4-pentylcyclohexyl)allyloxy]phenyl ester;
trans-4-pentylcyclohexanecarboxylic acid 4-[(E)-3-(trans-4-pentylcyclohexyl)allyloxy]phenyl ester, m.p. (C-$S_A$) 119° C., $S_A$-N 123° C., cl.p. (N-I) 156° C..

EXAMPLE 3

A solution of 0.5 g of 4-[(E)-3-(trans-4-pentylcyclohexyl)allyloxy]benzaldehyde and 0.3 g of 2-pentyl-1,3-propanediol in 50 ml of toluene was treated with 0.05 g
mixture was heated to of 4-toluenesulphonic acid. The boiling for 2,5 hours, with the resulting water being distilled off simultaneously. Then, 4 drops of triethylamine were added to the reaction mixture. After cooling the mixture was washed with 20 ml of 1N sodium hydrogen carbonate solution and twice with 20 ml of water each time, dried over sodium sulphate and concentrated. Chromatography of the residue on silica gel with toluene and recrystallization from ethyl acetate gave 0.15 g of trans-5-pentyl-2-(4-[(E)-3-(trans-4-pentylcyclohexyl)allyloxy]phenyl)-1,3-dioxane.

The 4-[(E)-3-(trans-4-pentylcyclohexyl)allyloxy]benzaldehyde used as the starting material was prepared as follows:

2.9 g of 4-hydroxybenzaldehyde, 5.0 g of (E)-3-(trans-4-pentylcyclohexyl)allyl alcohol, 4.1 g of diethyl azodicarboxylate, 6.2 g of triphenylphosphine and 100 ml of tetrahydrofuran were reacted in an analogous manner to Example 1 to give 4.5 g of 4-[(E)-3-(trans-4-pentylcyclohexyl)allyloxy]benzaldehyde (m.p. 54–55° C.).

The following compounds can be manufactured in an analogous manner:
trans-5-methyl-2-(4-[(E)-3-(trans-4-propylcyclohexyl)allyloxy]phenyl)-1,3-dioxane; hydrogen carbonate solution
trans-5-ethyl-2-(4-[(E)-3-(trans-4-propylcyclohexyl)allyloxy]phenyl)-1,3-dioxane;
trans-5-propyl-2-(4-[(E)-3-(trans-4-propylcyclohexyl)allyloxy]phenyl)-1,3-dioxane;
trans-5-butyl-2-(4-[(E)-3-(trans-4-propylcyclhexyl)allyloxy]phenyl)-1,3-dioxane;
trans-5-pentyl-2-(4-[(E)-3-(trans-4-propylcyclohexyl)allyloxy]phenyl)-1,3-dioxane;
trans-5-hexyl-2-(4-[(E)-3-(trans-4-propylcyclohexyl)allyloxy]phenyl)-1,3-dioxane;
trans-5-heptyl-2-(4-[(E)-3-(trans-4-Propylcyclohexyl)allyloxy]phenyl)-1,3-dioxane;
trans-5-methyl-2-(4-[(E)-3-(trans-4-pentylcyclohexyl)allyloxy]phenyl)-1,3-dioxane;
trans-5-ethyl-2-(4-[(E)(trans-4-pentylcylohexyl)allyloxy]phenyl)-1,3-dioxane;
trans-5-propyl-2-(4-[(E)-3-(trans-4-pentylcyclohexyl)allyloxy]phenyl)-1,3-dioxane;
trans-5-butyl-2-(4-[(E)-3-(trans-4-pentylcyclohexyl)allyloxy]phenyl)-1,3-dioxane;
trans-5-hexyl-2-(4-[(E)-3-(trans-4-pentylcyclohexyl)allyloxy]phenyl)-1,3-dioxane;
trans-5-heptyl-2-(4-[(E)-3-(trans-4-pentylcyclohexyl)allyloxy]phenyl)-1,3-dioxane.

EXAMPLE 4

1.4 g of 4-hydroxy-2-fluorobenzonitrile, 3.3 g of 4-[(E)-3-(trans-4-pentylcyclohexyl)allyloxy]benzoic acid, 2 5 g of N,N'-dicyclohexylcarbodiimide, 0.1 g of 4-(dimethylamino)pyridine and 100 ml of dichloromethane were reacted in an analogous manner to Example 2. This gave 1.5 g of 4-[(E)-3-(trans-4-pentylcyclohexyl)allyloxy]benzoic acid 4-cyano-3-fluorophenyl ester; m.p. (C-$S_A$) 54° C., $S_A$-N 68° C., cl.p. (N-I) 145° C..

The 4-[(E)-3-(trans-4-pentylcyclohexyl)allyloxy]benzoic acid used as the starting material was prepared as follows:

A solution of 4 g of 4-[(E)-3-(trans-4-pentylcyclohexyl)allyloxy]benzaldehyde (Prepared according to Example 3) in 100 ml of acetone was treated dropwise with 10 ml of Jones' reagent. The mixture was stirred at room temperature for 1 hour and then poured into 100 ml of water. The preciPitate which thereby resulted was filtered off, washed portionwise with water and dried in a vacuum. The crude product was recrystallized from ethanol and gave 2,5 g of pure 4-[(E)-3-(trans-4-pentylcyclohexyl)allyloxy]benzoic acid; m.p. 214–215° C..

The following compounds can be manufactured in an analogous manner. Those compounds shown with accompanying data actually were made.
4-[(E)-3-(trans-4-propylcyclohexyl)allyloxy]benzoic acid 4-cyano-3-fluorophenyl ester;
4-[(E)-3-(trans-4-pentylcyclohexyl)allyloxy]benzoic acid 3,4-difluorophenyl ester, m.p. (C-N) 93° C., $S_A$-N 88° C., cl.p. (N-I) 111° C.;
4-[(E)-3-(trans-4-Propylcyclohexyl)allyloxy]benzoic acid 4-cyano-2-fluorophenyl ester;
4-[(E)-3-(trans-4-pentylcyclohexyl)allyloxy]benzoic acid 4-cyano-2-fluorophenyl ester;
4-[(E)-3-(trans-4-heptylcyclohexyl)allyloxy]benzoic acid 4-cyano-2-fluorophenyl ester;
4-[(E)-3-(trans-4-pentylcyclohexyl)allyloxy]benzoic acid 4-fluorophenyl ester, m.p. (C-N) 105° C., $S_A$-N 102° C., cl.p. (N-I) 132° C.;
4-[(E)-3-(trans-4-pentylcyclohexyl)allyloxy]benzoic acid 4-chlorophenyl ester, m.p. (C-$S_A$) 131° C., $S_A$-N 135° C., cl.p. (N-I) 155° C.;
4-[(E)-3-(trans-4-pentylcyclohexyl)allyloxy]benzoic acid 4-bromophenyl ester, m.p. ) 136° C., $S_A$-N 145° C., cl.p. (N-I) 157° C.;
4-[(E)-3-(trans-4-pentylcyclohexyl)allyloxy]benzoic acid 4-iodophenyl ester, m.p. (C-$S_A$) 131° C., $S_A$-N 143° C., cl.p. (N-I) 152° C.;
4-[(E)-3-(trans-4-pentylcyclohexyl)allyloxy]benzoic acid 4-cyanophenyl ester, m.p. (C-N) 79° C., cl.p. (N-I) 170° C.;

4-[(E)-3-(trans-4-pentylcyclohexyl)allyloxy]benzoic acid 4-methylphenyl ester;
4-[(E)-3-(trans-4-pentylcyclohexyl)allyloxy]benzoic acid 4-ethylphenyl ester;
4-[(E)-3-(trans-4-pentylcylohexyl)alloxy]benzoic acid 4-propylphenyl ester;
4-[(E)-3-(trans-4-pentylcyclohexyl)allyloxy]benzoic acid 4-butylphenyl ester;
4-[(E)-3-(trans-4-pentylcyclohexyl)allyloxy]benzoic acid 4-pentylphenyl ester;
4-[(E)-3-(trans-4-pentylcyclohexyl)allyloxy]benzoic acid 4-methyl ester;
4-[(E)-3-(trans-4-pentylcyclohexyl)allyloxy]benzoic acid 4-ethyl ester;
4-[(E)-3-(trans-4-pentylcyclohexyl)allyloxy]benzoic acid 4-propyl ester;
4-[(E)-3-(trans-4-pentylcyclohexyl)allyloxy]benzoic acid 4-butyl ester;
4-[(E)-3-(trans-4-pentylcyclohexyl)allyloxy]benzoic acid 4-pentyl ester.

EXAMPLE 5

A mixture of 0.1 g of sodium hydride and 25 ml of tetrahydrofuran was treated with 0.5 g of trans-4-propylcyclohexanol while gassing with nitrogen, stirred for a further 2 hours, then treated with 1.0 g of (E)-3-(trans-4-pentylcyclohexyl)allyl bromide and subsequently heated to 70° C. overnight. Thereafter, the reaction mixture was treated with 500 ml of water and extracted four times with 50 ml of hexane each time. The combined organic phases were washed twice with 500 ml of water each time, dried over magnesium sulphate, filtered and then concentrated. The residue was purified by chromatography on silica gel with toluene. The trans-4-propylcyclohexyl (E)-3-(trans-4-pentylcyclohexyl)allyl ether obtained was recrystallized from acetone at −25° C.. This gave 1.2 g of pure product with m.p. (C-I) 26° C..

The (E)-3-(trans-4-pentylcyclohexyl)allyl bromide used as the starting material was prepared as follows:

A mixture of 9 g of (E)-3-(trans-4-pentylcyclohexyl)allyl alcohol, 12.3 g of triphenylphosphine and 50 ml of dichloromethane was treated portionwise within 10 minutes with 15.6 g of tetrabromomethane at −15° C. and while gassing with nitrogen. The reaction mixture was stirred at room temperature for 4 hours and then concentrated. The residue was suspended in 300 ml of hexane, the mixture was cooled to −20° C. and the Precipitate which thereby resulted was filtered off under suction. The filtrate was concentrated and the residue was purified by chromatography on silica gel with hexane. This gave 11 g of (E)-3-(trans-4-pentylcyclohexyl)allyl bromide.

The following compounds can be manufactured in an analogous manner. The compound shown with accompanying data actually was made.

trans-4-propylcyclohexyl (E)-3-(trans-4-methylcyclohexyl)allyl ether;
trans-4-propylcyclohexyl (E)-3-(trans-4-ethylcyclohexyl)allyl ether;
trans-4-propylcyclohexyl (E)-3-(trans-4-propylcyclohexyl)allyl ether;
trans-4-propylcyclohexyl (E)-3-(trans-4-butylcyclohexyl)allyl ether;
trans-4-propylcyclohexyl (E)-3-(trans-4-pentylcyclohexyl)allyl ether;
trans-4-propylcyclohexyl (E)-3-(trans-4-hexylcyclohexyl)allyl ether;
trans-4-propylcyclohexyl (E)-3-(trans-4-heptylcyclohexyl)allyl ether;
trans-4-pentylcyclohexyl (E)-3-(trans-4-methylcyclohexyl)allyl ether;
trans-4-pentylcyclohexyl (E)-3-(trans-4-ethylcyclohexyl)allyl ether;
trans-4-pentylcyclohexyl (E)-3-(trans-4-butylcyclohexyl)allyl ether;
trans-4-pentylcyclohexyl (E)-3-(trans-4-pentylcyclohexyl)allyl ether;
trans-4-pentylcyclohexyl (E)-3-(trans-4-hexylcyclohexyl)allyl ether;
trans-4-pentylcyclohexyl (E)-3-(trans-4-heptylcyclohexyl)allyl ether;
trans-4-(trans-4-propylcyclohexyl)cyclohexyl (E)-3-(trans4-propylcyclohexyl)allyl ether;
trans-4-(trans-4-propylcyclohexyl)cyclohexyl (E)-3-(trans-4-pentylcyclohexyl)allyl ether;
trans-4-[2-(trans-4-propylcyclohexyl)ethyl]cyclohexyl (E)-3-(trans-4-pentylcyclohexyl)allyl ether, m.p. (C-$S_B$) 58° C., cl.p. ($S_B$-I) 118° C.

EXAMPLE 6

A mixture of 4.5 g of trans-4-(trans-4-propylcyclohexyl)cyclohexanecarboxaldehyde, 5 g of ethyl diethylphosphonoacetate $(C_2H_5O)_2PCH_2COOC_2H_5$, 1.9 g of potassium hydroxide and 100 ml of tetrahydrofuran was stirred for 15 minutes and then treated with 500 ml of water and subsequently extracted three times with 100 ml of diethyl ether each time. The combined organic phases were washed twice with 500 ml of water each time, dried over magnesium sulphate, filtered and subsequently concentrated. The residue was purified by chromatography on silica gel with toluene. Recrystallization from acetone gave 1.8 g of pure (E)-3-[trans-4-(trans-4-propylcyclohexyl)cyclohexyl]acrylic acid ethyl ester with m.p. (C-N) 33° C. and cl.p. (N-I) 76° C..

The trans-4-(trans-4-propylcyclohexyl)cyclohexanecarboxaldehyde used as the starting material was prepared as follows:

A solution of 5 g of trans-4-(trans-4-propylcyclohexyl)cyclohexanecarbonitrile in 50 ml of dichloromethane was treated dropwise at −78° C. while gassing with nitrogen with 60 ml of a 20% solution (wt./vol.) of diisobutylaluminium hydride in hexane. The reaction mixture was stirred at room temperature for a further 2 hours, then treated with 500 ml of water and subsequently extracted four times with 200 ml of dichloromethane each time. The combined organic phases were washed twice with 500 ml of water, dried over magnesium sulphate, filtered and subsequently concentrated. This gave 4.5 g of trans-4-(trans-4-propylcyclohexyl)cyclohexanecarboxaldehyde.

The following compounds can be manufactured in an analogous manner. The compound shown with accompanying data actually was made.

(E)-3-[trans-4-(trans-4-propylcyclohexyl)cyclohexyl]acrylic acid methyl ester;
(E)-3-[trans-4-(trans-4-propylcyclohexyl)cyclohexyl]acrylic acid propyl ester;
(E)-3-[trans-4-(trans-4-propylcyclohexyl)cyclohexyl]acrylic acid butyl ester;
(E)-3-[trans-4-(trans-4-propylcyclohexyl)cyclohexyl]acrylic acid pentyl ester;
(E)-3-[trans-4-(trans-4-butylcyclohexyl)cyclohexyl]acrylic acid methyl ester;
(E)-3-[trans-4-(trans-4-butylcyclohexyl)cyclohexyl]acrylic acid ethyl ester;

(E)-3-[trans-4-(trans-4-butylcyclohexyl)cyclohexyl]acrylic acid propyl ester;
(E)-3-[trans-4-(trans-4-butylcyclohexyl)cyclohexyl]acrylic acid butyl ester;
(E)-3-[trans-4-(trans-4-butylcyclohexyl)cyclohexyl]acrylic acid pentyl ester;
(E)-3-[trans-4-(trans-4-pentylcyclohexyl)cyclohexyl]acrylic acid methyl ester;
(E)-3-[trans-4-(trans-4-pentylcyclohexyl)cyclohexyl]-acrylic acid ethyl ester, m.p. (C-S$_b$) 27° C., S$_b$-N 49° C., cl.p. (N-I) 93° C.;
(E)-3-[trans-4-(trans-4-pentylcyclohexyl)cyclohexyl]acrylic acid propyl ester;
(E)-3-[trans-4-(trans-4-pentylcyclohexyl)cyclohexyl] acrylic acid butyl ester;
(E)-3-[trans-4-(trans-4-pentylcyclohexyl)cyclohexyl] acrylic acid pentyl ester.

I claim:

1. A compound of the formula

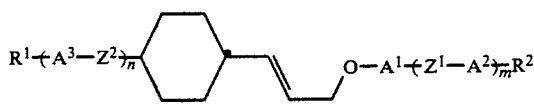

wherein $R^1$ is $R^3$ or $R^3$—$A^4$—$Z^3$—and $R^2$ is $R^4$ or —$Z^4$—$A^5$ $R^4$; each of m and n individually is the integer 0 or 1; each of $A^1$, $A^2$, $A^3$, $A^4$ and $A^5$ independently is 1,4-phenylene which is unsubstituted or substituted with one or more of halogen, cyano or methyl, said unsubstituted or substituted 1,4-phenylene as defined above wherein one of irs CH group or two CH groups are replaced by nitrogen, trans-1,4-cyclohexylene, trans-1,4-cyclohexylene in which two non-adjacent methylene groups are replaced by at least one of oxygen or sulphur, 1-cyano-trans-1,4-cyclohexylene, bicyclo[2.2.2]octane-14-diyl, naphthalene-2,6-diyl, tetralin-2,6-diyl or t[ans-decalin-2,6-diyl; each of $Z^1$, $Z^2$, $Z^3$ and $Z^4$ independently is a single covalent bond, COO—, —OOC—, —CH$_2$O—, —OCH$_2$—, —CH$_2$CH$_2$—, —C≡C—, —(CH$_2$)$_3$O—, —O(CH$_2$)$_3$— or the trans configuration of either —CH=CH—CH$_2$O— or —OCH$_2$—CH=CH—; each of $R^3$ and $R^4$ independently is halogen, cyano, —NCS, —CF$_3$, —OCF$_3$, alkyl or alkyl in which one or more of its carbon atoms are replaced as follows: one >CH—CH< is replaced by >C=C<, one methylene group or two non-adjacent methylene groups are replaced by at least one of —O—, —COO— and —OOC—, or one methylene group is replaced by —CHX—; and X is halogen, cyano or methyl.

2. The compound of claim 1, wherein $A^1$ is 1,4-phenylene which is unsubstituted or substituted with one or more of halogen, cyano or methyl, or trans-1,4-cyclohexylene.

3. The compound of claim 1 of the formula

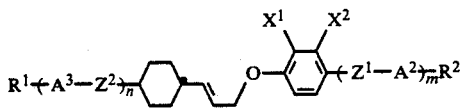

wherein each of $X^1$ and $X^2$ independently is hydrogen, halogen, cyano or methyl; and $A^2$, $A^3$, $R^1$, $R^2$, $Z^1$, $Z^2$, m and n have the above significances.

4. The compound of claim 1, wherein $A^3$ is trans-1,4-cyclohexylene, $Z^2$ is a single covalent bond or —CH$_2$CH$_2$—, and n is the integer 0 or 1.

5. The compound of claim 1, wherein each of $Z^1$, $Z^2$, $Z^3$ and $Z^4$ is a single covalent bond or one of the groups $Z^1$, $Z^2$, $Z^3$ and $Z^4$ also is —COO—, —OOC—, —CH$_2$O—, —OCH$_2$—, —CH$_2$CH$_2$—, —C≡C—, —(CH$_2$)$_3$O—, —O(CH$_2$)$_3$— or the trans configuration of either —CH=CH—CH$_2$O— or —OCH$_2$—CH=CH—.

6. The compound of claim 1 of the formula

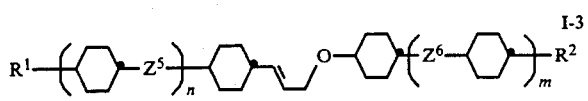

wherein each of $Z^5$ and $Z^6$ independently is a single covalent bond or —CH$_2$CH$_2$— and $R^1$, $R^2$, m and n have the above significances.

7. The compound of claim 1, wherein $R^1$ is a group $R^3$, $R^2$ is a group $R^4$ and either m and n is the integer 0 such that m is the integer 1 and n is the integer 0 or m is the integer 0 and n is the integer 1 or both m and n are the integer 0.

8. The compound of claim 1, of the formula

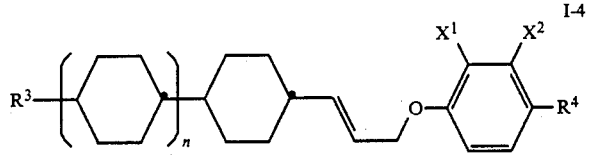

wherein n is the integer 0 or 1; each of $X^1$ and $X^2$, independently is hydrogen, halogen, cyano or methyl; and $R^3$ and $R^4$ have the above significances.

9. The compound of claim 1, of the formula

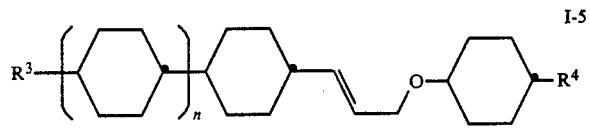

wherein n is the integer 0 or 1; and $R^3$ and $R^4$ have the above significances.

10. The compound of claim 1, of the formula

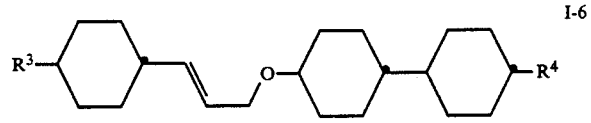

wherein $R^3$ and $R^4$ have the above significances.

11. The compound of claim 1, of the formula

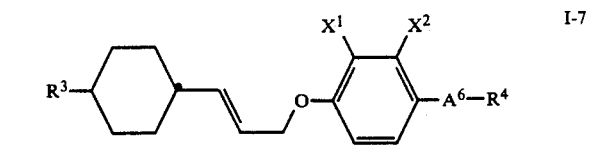

wherein each of $X^1$ and $X^2$ independently is hydrogen, halogen, cyano or methyl; $A^6$ is 1,4-phenylene, pyridine-2,5-diyl, pyrimidine-2,5-diyl, pyrazine-2,5-diyl, trans.1,4-cyclohexylene, trans-1.3- -dioxane-2,5-diyl or trans-decalin-2,6-diyl: and $R^3$ and $R^4$ have the above significances.

12. The compound of claim 1, of the formula

UNITED STATES PATENT AND TRADEMARK OFFICE
CERTIFICATE OF CORRECTION

PATENT NO. : 5,032,312
DATED : July 16, 1991
INVENTOR(S) : STEPHEN KELLY

It is certified that error appears in the above-identified patent and that said Letters Patent is hereby corrected as shown below:

Claim 1, column 29, line 26, delete "$R^1$ 1 is $R^3$" and insert therefor -- $R^1$ is $R^3$ --;

Claim 1, column 29, line 33, delete "irs" and insert therefor -- its --;

Claim 1, column 29, line 39, delete "t[ans-decalin-2,6-diyl" and insert therefor -- trans-decalin-2,6-diyl --;

Claim 1, column 29, line 40, delete "COO-" and insert therefor -- -COO- --;

Claim 1, column 29, line 41, delete "-$CH_{20}$-" and insert therefor -- -$CH_2O$- --;

Claim 7, column 30, line 17, delete "$R^1$ 1 is a group $R^3$" and insert therefor -- $R^1$ is a group $R^3$ --;

Claim 11, column 30, line 65, delete "trans.1,4-cyclohexylene" and insert therefor -- trans-1,4-cyclohexylene --;

Claim 11, column 30, line 65, delete "trans-1,3- -dioxane-2,5-diyl" and insert therefor -- trans-1,3-dioxane-2,5-diyl --;

Claim 11, column 30, line 66, delete "trans-decalin-2,6-diyl:" and insert therefor -- trans-decalin-2,6-diyl; --;

Claim 13, column 31, line 23, between "-C≡C-" and "-$OCH_2$-CH=" insert -- -$O(CH_2)_3$- or the trans configuration of --;

Claim 14, column 31, line 28, between "halogen" and "cyano" insert -- , --;

Claim 18, column 31, line 51, between "each of m and n" and "$A^1$, $A^2$, $A^3$, $A^4$, and $A^5$" insert -- individually is the integer 0 or 1; each of --;

UNITED STATES PATENT AND TRADEMARK OFFICE
CERTIFICATE OF CORRECTION

PATENT NO. : 5,032,312
DATED : July 16, 1991
INVENTOR(S) : STEPHEN KELLY

It is certified that error appears in the above-identified patent and that said Letters Patent is hereby corrected as shown below:

Claim 19, column 32, line 24, delete "$R^1$ 1 is $R^3$" and insert therefor -- $R^1$ is $R^3$ --;

Claim 19, column 32, line 43, between "is" and "in" insert -- halogen, cyano, -NCS, $-CF_3$, $-OCF_3$, alkyl or alkyl --;

Signed and Sealed this

Twenty-seventh Day of October, 1992

Attest:

DOUGLAS B. COMER

Attesting Officer

Acting Commissioner of Patents and Trademarks